US009468487B2

(12) United States Patent
Shadduck et al.

(10) Patent No.: US 9,468,487 B2
(45) Date of Patent: *Oct. 18, 2016

(54) MEDICAL INSTRUMENT AND METHOD OF USE

(71) Applicant: Tsunami MedTech, LLC, Menlo Park, CA (US)

(72) Inventors: John H. Shadduck, Menlo Park, CA (US); Michael Hoey, Shoreview, MN (US)

(73) Assignee: Tsunami MedTech, LLC, Menlo Park, CA (US)

( * ) Notice: Subject to any disclaimer, the term of this patent is extended or adjusted under 35 U.S.C. 154(b) by 358 days.

This patent is subject to a terminal disclaimer.

(21) Appl. No.: 13/872,669

(22) Filed: Apr. 29, 2013

(65) Prior Publication Data
US 2013/0237978 A1 Sep. 12, 2013

Related U.S. Application Data

(60) Division of application No. 11/329,381, filed on Jan. 10, 2006, now Pat. No. 8,444,636, and a
(Continued)

(51) Int. Cl.
*A61B 18/14* (2006.01)
*A61B 18/04* (2006.01)
*A61B 18/00* (2006.01)

(52) U.S. Cl.
CPC ............. *A61B 18/042* (2013.01); *A61B 18/04* (2013.01); *A61B 2018/0063* (2013.01); *A61B 2018/00619* (2013.01); *A61B 2018/046* (2013.01); *A61B 2018/048* (2013.01)

(58) Field of Classification Search
CPC ................ A61B 18/042; A61B 18/04; A61B 2018/0063; A61B 2018/046; A61B 2018/048; A61B 2018/00619
See application file for complete search history.

(56) References Cited

U.S. PATENT DOCUMENTS

| 408,899 A | 8/1889 | Bioch et al. |
| 697,181 A | 4/1902 | Smith |

(Continued)

FOREIGN PATENT DOCUMENTS

| WO | WO 00/11927 | 3/2000 |
| WO | WO 00/29055 | 5/2000 |

(Continued)

OTHER PUBLICATIONS

Coda, et al., "Effects of pulmonary reventilation on gas exchange after cryolytic disobstruction of endobronchial tumors:" *Minerva Medical*, vol. 72, pp. 1627-1631, Jun. 1981 (with English translation).

(Continued)

*Primary Examiner* — Michael Peffley
(74) *Attorney, Agent, or Firm* — Levine Bagade Han LLP

(57) ABSTRACT

An instrument for thermally-mediated therapies in targeted tissue volumes or for volumetric removal of tissue. In one embodiment, the instrument has an interior chamber that includes a diffuser structure for diffusing a biocompatible conductive fluid that is introduced under high pressure. The interior chamber further includes surfaces of opposing polarity electrodes for vaporizing the small cross-section diffused fluid flows created within a diffuser structure. In one embodiment, the diffuser structure includes a negative temperature coefficient of resistance material between the opposing polarity surfaces. The NTCR structure can self-adjust the lengths of current paths between the opposing polarities to insure complete vaporization of the volume of flow of conductive fluid. The non-ionized vapor phase media is ejected from a working surface of the instrument and a controlled vapor-to-liquid phase chance in an interface with tissue applies thermal energy substantially equal to the heat of vaporization to ablate tissue. In another embodiment, the instrument provides voltage means for converting the non-ionized vapor phase media into an ionized media or plasma for applying energy to body structure.

7 Claims, 32 Drawing Sheets

Related U.S. Application Data continuation-in-part of application No. 10/681,625, filed on Oct. 7, 2003, now Pat. No. 7,674,259, which is a continuation-in-part of application No. 10/017,582, filed on Dec. 7, 2001, now Pat. No. 6,669,694, said application No. 11/329,381 is a continuation-in-part of application No. 11/158,930, filed on Jun. 22, 2005, now Pat. No. 7,892,229, and a continuation-in-part of application No. 11/244,329, filed on Oct. 5, 2005, now Pat. No. 8,016,823.

(60) Provisional application No. 60/643,045, filed on Jan. 11, 2005.

(56) References Cited

U.S. PATENT DOCUMENTS

| | | |
|---|---|---|
| 1,719,750 A | 9/1927 | Bridge et al. |
| 3,818,913 A | 6/1974 | Wallach |
| 3,880,168 A | 4/1975 | Berman |
| 3,930,505 A | 1/1976 | Wallach |
| 4,024,866 A | 5/1977 | Wallach |
| 4,083,077 A | 4/1978 | Knight et al. |
| 4,672,962 A | 6/1987 | Hershenson |
| 4,682,596 A | 7/1987 | Bales et al. |
| 4,748,979 A | 6/1988 | Hershenson |
| 4,773,410 A | 9/1988 | Blackmer et al. |
| 4,793,352 A | 12/1988 | Eichenlaub |
| 4,872,920 A | 10/1989 | Flynn et al. |
| 4,898,574 A | 2/1990 | Uchiyama et al. |
| 4,915,113 A | 4/1990 | Holman |
| 4,941,475 A | 7/1990 | Williams et al. |
| 4,950,266 A | 8/1990 | Sinofsky |
| 4,985,027 A | 1/1991 | Dressel |
| 5,006,119 A | 4/1991 | Acker et al. |
| 5,011,566 A | 4/1991 | Hoffman |
| 5,078,736 A | 1/1992 | Behl |
| 5,084,043 A | 1/1992 | Hertzmann et al. |
| 5,102,410 A | 4/1992 | Dressel |
| 5,112,328 A | 5/1992 | Taboada et al. |
| 5,122,138 A * | 6/1992 | Manwaring ........ A61B 18/1482 606/46 |
| 5,158,536 A | 10/1992 | Sekins et al. |
| 5,162,374 A | 11/1992 | Mulieri et al. |
| 5,190,539 A | 3/1993 | Fletcher et al. |
| 5,217,459 A | 6/1993 | Kamerling |
| 5,217,465 A | 6/1993 | Steppe |
| 5,263,951 A | 11/1993 | Spears et al. |
| 5,277,696 A | 1/1994 | Hagen |
| 5,298,298 A | 3/1994 | Hoffman |
| 5,318,014 A | 6/1994 | Carter |
| 5,331,947 A | 7/1994 | Shturman |
| 5,334,190 A | 8/1994 | Seiler |
| 5,344,397 A | 9/1994 | Heaven et al. |
| 5,348,551 A | 9/1994 | Spears et al. |
| 5,352,512 A | 10/1994 | Hoffman |
| 5,417,686 A | 5/1995 | Peterson et al. |
| 5,424,620 A | 6/1995 | Cheon et al. |
| 5,433,708 A | 7/1995 | Nichols et al. |
| 5,433,739 A | 7/1995 | Sluijter |
| 5,462,521 A | 10/1995 | Brucker et al. |
| 5,500,012 A | 3/1996 | Brucker et al. |
| 5,503,638 A | 4/1996 | Cooper et al. |
| 5,505,730 A | 4/1996 | Edwards |
| 5,524,620 A | 6/1996 | Rosenschein |
| 5,529,076 A | 6/1996 | Schachar |
| 5,542,928 A | 8/1996 | Evans et al. |
| 5,549,628 A | 8/1996 | Cooper et al. |
| 5,554,172 A | 9/1996 | Horner et al. |
| 5,562,608 A | 10/1996 | Sekins et al. |
| 5,575,803 A | 11/1996 | Cooper et al. |
| 5,584,872 A | 12/1996 | LaFontaine et al. |
| 5,591,157 A | 1/1997 | Hennings et al. |
| 5,591,162 A | 1/1997 | Fletcher et al. |
| 5,616,120 A | 4/1997 | Andrew et al. |
| 5,620,440 A | 4/1997 | Heckele et al. |
| 5,647,871 A | 7/1997 | Levine et al. |
| 5,653,692 A | 8/1997 | Masterson et al. |
| 5,662,671 A | 9/1997 | Barbut et al. |
| 5,669,907 A | 9/1997 | Platt, Jr. et al. |
| 5,681,282 A | 10/1997 | Eggers et al. |
| 5,683,366 A | 11/1997 | Eggers et al. |
| 5,695,507 A | 12/1997 | Auth et al. |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,700,262 A | 12/1997 | Acosta et al. |
| 5,707,352 A | 1/1998 | Sekins et al. |
| 5,735,811 A | 4/1998 | Brisken |
| 5,741,247 A | 4/1998 | Rizoiu et al. |
| 5,741,248 A | 4/1998 | Stern et al. |
| 5,752,965 A | 5/1998 | Francis et al. |
| 5,755,753 A | 5/1998 | Knowlton |
| 5,769,880 A | 6/1998 | Truckai et al. |
| 5,782,914 A | 7/1998 | Schankereli |
| 5,785,521 A | 7/1998 | Rizoiu et al. |
| 5,800,482 A | 9/1998 | Pomeranz et al. |
| 5,810,764 A | 9/1998 | Eggers et al. |
| 5,824,703 A | 10/1998 | Clark, Jr. |
| 5,827,268 A | 10/1998 | Laufer |
| 5,836,896 A | 11/1998 | Rosenschein |
| 5,843,019 A | 12/1998 | Eggers et al. |
| 5,843,073 A | 12/1998 | Sinofsky |
| 5,871,469 A | 2/1999 | Eggers et al. |
| 5,879,329 A | 3/1999 | Ginsburg |
| 5,885,243 A | 3/1999 | Capetan et al. |
| 5,888,198 A | 3/1999 | Eggers et al. |
| 5,891,095 A | 4/1999 | Eggers et al. |
| 5,891,134 A | 4/1999 | Goble et al. |
| 5,911,734 A | 6/1999 | Tsugita et al. |
| 5,913,856 A | 6/1999 | Chia et al. |
| 5,944,686 A | 8/1999 | Patterson et al. |
| 5,944,715 A * | 8/1999 | Goble ................ A61B 18/148 604/21 |
| 5,957,919 A | 9/1999 | Laufer |
| 5,964,752 A * | 10/1999 | Stone .................... A61B 18/04 606/27 |
| 5,968,037 A | 10/1999 | Rizoiu |
| 5,980,504 A | 11/1999 | Sharkey et al. |
| 5,986,662 A | 11/1999 | Argiro et al. |
| 5,989,212 A | 11/1999 | Sussman et al. |
| 5,989,238 A | 11/1999 | Ginsburg |
| 5,989,249 A | 11/1999 | Kirwan |
| 5,989,445 A | 11/1999 | Wise et al. |
| 5,997,499 A | 12/1999 | Sussman et al. |
| 6,024,095 A | 2/2000 | Stanley, III |
| 6,024,733 A | 2/2000 | Eggers et al. |
| 6,027,501 A | 2/2000 | Goble et al. |
| 6,032,077 A | 2/2000 | Pomeranz |
| 6,032,674 A | 3/2000 | Eggers et al. |
| 6,047,700 A | 4/2000 | Eggers et al. |
| 6,053,909 A | 4/2000 | Shadduck |
| 6,056,746 A | 5/2000 | Goble et al. |
| 6,059,011 A | 5/2000 | Giolo |
| 6,063,079 A | 5/2000 | Hovda et al. |
| 6,063,081 A | 5/2000 | Mulier et al. |
| 6,066,134 A | 5/2000 | Eggers et al. |
| 6,066,139 A | 5/2000 | Ryan et al. |
| 6,074,358 A | 6/2000 | Andrew et al. |
| 6,080,128 A | 6/2000 | Sussman et al. |
| 6,080,151 A | 6/2000 | Swartz et al. |
| 6,083,255 A | 7/2000 | Laufer et al. |
| 6,095,149 A | 8/2000 | Sharkey et al. |
| 6,099,251 A | 8/2000 | LaFleur |
| 6,102,046 A | 8/2000 | Weinstein et al. |
| 6,102,885 A | 8/2000 | Bass |
| 6,106,516 A | 8/2000 | Massengill |
| 6,110,162 A | 8/2000 | Sussman et al. |
| 6,113,722 A | 9/2000 | Hoffman et al. |
| 6,126,682 A | 10/2000 | Sharkey et al. |
| 6,130,671 A | 10/2000 | Argiro |
| 6,139,571 A | 10/2000 | Fuller et al. |
| 6,149,620 A | 11/2000 | Baker et al. |

(56) References Cited

U.S. PATENT DOCUMENTS

| | | | |
|---|---|---|---|
| 6,156,036 A | 12/2000 | Sussman et al. |
| 6,159,194 A | 12/2000 | Eggers et al. |
| 6,162,232 A | 12/2000 | Shadduck |
| 6,168,594 B1 | 1/2001 | LaFontaine et al. |
| 6,174,308 B1 | 1/2001 | Goble et al. |
| 6,179,805 B1 | 1/2001 | Sussman et al. |
| 6,190,381 B1 | 2/2001 | Olsen et al. |
| 6,194,066 B1 | 2/2001 | Hoffman |
| 6,196,989 B1 | 3/2001 | Padget et al. |
| 6,200,333 B1 | 3/2001 | Laufer |
| 6,206,848 B1 | 3/2001 | Sussman et al. |
| 6,210,404 B1 | 4/2001 | Shadduck |
| 6,210,405 B1 | 4/2001 | Goble et al. |
| 6,219,059 B1 | 4/2001 | Argiro |
| 6,224,592 B1 | 5/2001 | Eggers et al. |
| 6,231,567 B1 | 5/2001 | Rizoiu et al. |
| 6,235,020 B1 | 5/2001 | Cheng et al. |
| 6,238,391 B1 | 5/2001 | Olsen et al. |
| 6,254,597 B1 | 7/2001 | Rizoiu et al. |
| 6,261,286 B1 | 7/2001 | Goble et al. |
| 6,261,311 B1 | 7/2001 | Sharkey et al. |
| 6,264,650 B1 | 7/2001 | Hovda et al. |
| 6,264,651 B1 | 7/2001 | Underwood et al. |
| 6,264,654 B1 | 7/2001 | Swartz et al. |
| 6,277,112 B1 | 8/2001 | Underwood et al. |
| 6,283,910 B1 | 9/2001 | Bradshaw et al. |
| 6,283,961 B1 | 9/2001 | Underwood et al. |
| 6,283,989 B1 | 9/2001 | Laufer et al. |
| 6,287,274 B1 | 9/2001 | Sussman et al. |
| 6,290,715 B1 | 9/2001 | Sharkey et al. |
| 6,296,636 B1 | 10/2001 | Cheng et al. |
| 6,296,638 B1 | 10/2001 | Davison et al. |
| 6,299,633 B1 | 10/2001 | Laufer |
| 6,300,150 B1 | 10/2001 | Venkatasubramanian |
| 6,312,408 B1 | 11/2001 | Eggers et al. |
| 6,312,474 B1 | 11/2001 | Francis et al. |
| 6,315,755 B1 | 11/2001 | Sussman |
| 6,319,222 B1 | 11/2001 | Andrew et al. |
| 6,327,505 B1 | 12/2001 | Medhkour et al. |
| 6,331,171 B1 | 12/2001 | Cohen |
| 6,355,032 B1 | 3/2002 | Hovda et al. |
| 6,375,635 B1 | 4/2002 | Moutafis et al. |
| 6,379,350 B1 | 4/2002 | Sharkey et al. |
| 6,391,025 B1 | 5/2002 | Weinstein et al. |
| 6,394,949 B1 | 5/2002 | Crowley et al. |
| 6,394,996 B1 | 5/2002 | Lawrence et al. |
| 6,398,759 B1 | 6/2002 | Sussman et al. |
| 6,398,775 B1 | 6/2002 | Perkins et al. |
| 6,409,723 B1 | 6/2002 | Edwards |
| 6,416,508 B1 | 7/2002 | Eggers et al. |
| 6,458,231 B1 | 10/2002 | Wapner et al. |
| 6,461,350 B1 | 10/2002 | Underwood et al. |
| 6,464,694 B1 | 10/2002 | Massengil |
| 6,464,695 B2 | 10/2002 | Hovda et al. |
| 6,468,270 B1 | 10/2002 | Hovda et al. |
| 6,468,274 B1 | 10/2002 | Alleyne et al. |
| 6,468,313 B1 | 10/2002 | Claeson et al. |
| 6,475,215 B1 * | 11/2002 | Tanrisever ............... H05H 1/24 606/32 |
| 6,482,201 B1 | 11/2002 | Olsen et al. |
| 6,482,202 B1 | 11/2002 | Goble et al. |
| 6,488,673 B1 | 12/2002 | Laufer et al. |
| 6,493,589 B1 | 12/2002 | Medhkour et al. |
| 6,500,173 B2 | 12/2002 | Underwood et al. |
| 6,508,816 B2 | 1/2003 | Shadduck |
| 6,517,533 B1 | 2/2003 | Swaminathan |
| 6,517,568 B1 | 2/2003 | Sharkey et al. |
| 6,522,930 B1 | 2/2003 | Schaer et al. |
| 6,527,761 B1 | 3/2003 | Buch et al. |
| 6,527,766 B1 | 3/2003 | Bair |
| 6,540,741 B1 | 4/2003 | Underwood et al. |
| 6,544,211 B1 | 4/2003 | Andrew et al. |
| 6,544,248 B1 | 4/2003 | Bass |
| 6,547,810 B1 | 4/2003 | Sharkey et al. |
| 6,558,379 B1 | 5/2003 | Batchelor et al. |
| 6,569,146 B1 | 5/2003 | Werner et al. |
| 6,575,929 B2 | 6/2003 | Sussman et al. |
| 6,575,933 B1 | 6/2003 | Wittenberger et al. |
| 6,575,968 B1 | 6/2003 | Eggers et al. |
| 6,579,270 B2 | 6/2003 | Sussman et al. |
| 6,582,423 B1 | 6/2003 | Thapliyal et al. |
| 6,585,639 B1 | 7/2003 | Kotmel et al. |
| 6,588,613 B1 | 7/2003 | Pechenik et al. |
| 6,589,201 B1 | 7/2003 | Sussman et al. |
| 6,589,204 B1 | 7/2003 | Sussman et al. |
| 6,592,594 B2 | 7/2003 | Rimbaugh et al. |
| 6,595,990 B1 | 7/2003 | Weinstein et al. |
| 6,599,311 B1 | 7/2003 | Biggs et al. |
| 6,602,248 B1 | 8/2003 | Sharps et al. |
| 6,605,087 B2 | 8/2003 | Swartz et al. |
| 6,610,043 B1 | 8/2003 | Ingenito |
| 6,620,130 B1 | 9/2003 | Ginsburg |
| 6,620,155 B2 | 9/2003 | Underwood et al. |
| 6,623,444 B2 | 9/2003 | Babaev |
| 6,632,193 B1 | 10/2003 | Davison et al. |
| 6,632,220 B1 | 10/2003 | Eggers et al. |
| 6,634,363 B1 | 10/2003 | Danek et al. |
| 6,648,847 B2 | 11/2003 | Sussman et al. |
| 6,652,594 B2 | 11/2003 | Francis et al. |
| 6,653,525 B2 | 11/2003 | Ingenito et al. |
| 6,659,106 B1 | 12/2003 | Hovda et al. |
| 6,669,685 B1 | 12/2003 | Rizoiu et al. |
| 6,669,694 B2 | 12/2003 | Shadduck |
| 6,676,628 B2 | 1/2004 | Sussman et al. |
| 6,676,629 B2 | 1/2004 | Andrew et al. |
| 6,679,264 B1 | 1/2004 | Deem et al. |
| 6,679,879 B2 | 1/2004 | Shadduck |
| 6,682,520 B2 | 1/2004 | Ingenito |
| 6,692,494 B1 | 2/2004 | Cooper et al. |
| 6,695,839 B2 | 2/2004 | Sharkey et al. |
| 6,699,212 B1 | 3/2004 | Kadziauskas et al. |
| 6,699,244 B2 | 3/2004 | Carranza et al. |
| 6,712,811 B2 | 3/2004 | Underwood et al. |
| 6,712,812 B2 | 3/2004 | Roschak et al. |
| 6,719,738 B2 | 4/2004 | Mehier |
| 6,719,754 B2 | 4/2004 | Underwood et al. |
| 6,723,064 B2 | 4/2004 | Babaev |
| 6,726,684 B1 | 4/2004 | Woloszko et al. |
| 6,726,708 B2 | 4/2004 | Lasheras |
| 6,746,447 B2 | 6/2004 | Davison et al. |
| 6,755,794 B2 | 6/2004 | Soukup |
| 6,758,846 B2 | 7/2004 | Goble et al. |
| 6,763,836 B2 | 7/2004 | Tasto et al. |
| 6,764,487 B2 | 7/2004 | Mulier et al. |
| 6,766,202 B2 | 7/2004 | Underwood et al. |
| 6,770,070 B1 | 8/2004 | Balbierz |
| 6,770,071 B2 | 8/2004 | Woloszko et al. |
| 6,772,012 B2 | 8/2004 | Ricart et al. |
| 6,776,765 B2 | 8/2004 | Soukup et al. |
| 6,780,180 B1 | 8/2004 | Goble et al. |
| 6,805,130 B2 | 10/2004 | Tasto et al. |
| 6,832,996 B2 | 12/2004 | Woloszko et al. |
| 6,837,884 B2 | 1/2005 | Woloszko |
| 6,837,888 B2 | 1/2005 | Ciarrocca et al. |
| 6,852,108 B2 | 2/2005 | Barry et al. |
| 6,860,847 B2 | 3/2005 | Alferness et al. |
| 6,860,868 B2 | 3/2005 | Sussman et al. |
| 6,875,194 B2 | 4/2005 | MacKool |
| 6,896,674 B1 | 5/2005 | Woloszko et al. |
| 6,896,675 B2 | 5/2005 | Leung et al. |
| 6,896,690 B1 | 5/2005 | Lambrecht et al. |
| 6,901,927 B2 | 6/2005 | Deem et al. |
| 6,904,909 B2 | 6/2005 | Andreas et al. |
| 6,907,881 B2 | 6/2005 | Suki et al. |
| 6,911,028 B2 | 6/2005 | Shadduck |
| 6,918,903 B2 | 7/2005 | Bass |
| 6,921,385 B2 | 7/2005 | Clements et al. |
| 6,929,640 B1 | 8/2005 | Underwood et al. |
| 6,949,096 B2 | 9/2005 | Davison et al. |
| 6,955,675 B2 | 10/2005 | Jain |
| 6,960,182 B2 | 11/2005 | Moutafis et al. |
| 6,962,584 B1 | 11/2005 | Stone et al. |
| 6,972,014 B2 | 12/2005 | Eum et al. |
| 6,978,174 B2 | 12/2005 | Gelfand et al. |

(56) References Cited

U.S. PATENT DOCUMENTS

| | | | |
|---|---|---|---|
| 6,986,769 B2 | 1/2006 | Nelson et al. |
| 6,991,028 B2 | 1/2006 | Comeaux et al. |
| 6,991,631 B2 | 1/2006 | Woloszko et al. |
| 7,022,088 B2 | 4/2006 | Keast et al. |
| 7,031,504 B1 | 4/2006 | Argiro et al. |
| 7,083,612 B2 | 8/2006 | Littrup et al. |
| 7,128,748 B2 | 10/2006 | Mooradian et al. |
| 7,136,064 B2 | 11/2006 | Zuiderveld |
| 7,144,402 B2 | 12/2006 | Kuester, III |
| 7,144,588 B2 | 12/2006 | Oray et al. |
| 7,162,303 B2 | 1/2007 | Levin et al. |
| 7,192,400 B2 | 3/2007 | Campbell et al. |
| 7,233,820 B2 | 6/2007 | Gilboa |
| 7,235,070 B2 | 6/2007 | Vanney |
| 7,335,195 B2 | 2/2008 | Mehier |
| 7,347,859 B2 | 3/2008 | Garabedian et al. |
| 7,549,987 B2 | 6/2009 | Shadduck |
| 7,585,295 B2 * | 9/2009 | Ben-Nun ............ A61B 18/082 606/28 |
| 7,617,005 B2 | 11/2009 | Demarais et al. |
| 7,620,451 B2 | 11/2009 | Demarais et al. |
| 7,647,115 B2 | 1/2010 | Levin et al. |
| 7,653,438 B2 | 1/2010 | Deem et al. |
| 7,674,259 B2 | 3/2010 | Shadduck |
| 7,717,948 B2 | 5/2010 | Demarais et al. |
| 7,756,583 B2 | 7/2010 | Demarais et al. |
| 7,815,616 B2 | 10/2010 | Boehringer et al. |
| 7,853,333 B2 | 12/2010 | Demarais |
| 7,873,417 B2 | 1/2011 | Demarais et al. |
| 7,892,229 B2 | 2/2011 | Shadduck et al. |
| 7,937,143 B2 | 5/2011 | Demarais et al. |
| 7,993,323 B2 | 8/2011 | Barry et al. |
| 8,016,823 B2 | 9/2011 | Shadduck |
| 8,131,371 B2 | 3/2012 | Demarals et al. |
| 8,131,372 B2 | 3/2012 | Levin et al. |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,187,269 B2 | 5/2012 | Shadduck et al. |
| 8,192,424 B2 | 6/2012 | Woloszko |
| 8,313,485 B2 | 11/2012 | Shadduck |
| 8,444,636 B2 | 5/2013 | Shadduck et al. |
| 8,574,226 B2 | 11/2013 | Shadduck |
| 8,579,888 B2 | 11/2013 | Hoey et al. |
| 8,579,892 B2 | 11/2013 | Hoey et al. |
| 8,579,893 B2 | 11/2013 | Hoey |
| 9,113,944 B2 | 8/2015 | Shadduck |
| 2001/0020167 A1 | 9/2001 | Woloszko et al. |
| 2001/0029370 A1 | 10/2001 | Hodva et al. |
| 2001/0037106 A1 | 11/2001 | Shadduck |
| 2002/0049438 A1 | 4/2002 | Sharkey et al. |
| 2002/0077516 A1 | 6/2002 | Flanigan |
| 2002/0078956 A1 | 6/2002 | Sharpe et al. |
| 2002/0082667 A1 | 6/2002 | Shadduck |
| 2002/0095152 A1 | 7/2002 | Ciarrocca et al. |
| 2002/0111386 A1 | 8/2002 | Sekins et al. |
| 2002/0133147 A1 | 9/2002 | Marchitto et al. |
| 2002/0151917 A1 | 10/2002 | Barry |
| 2002/0161326 A1 | 10/2002 | Sussman et al. |
| 2002/0173815 A1 | 11/2002 | Hogendijk et al. |
| 2002/0177846 A1 | 11/2002 | Mulier et al. |
| 2002/0193789 A1 | 12/2002 | Underwood et al. |
| 2003/0028189 A1 | 2/2003 | Woloszko et al. |
| 2003/0040742 A1 | 2/2003 | Underwood et al. |
| 2003/0097126 A1 | 5/2003 | Woloszko et al. |
| 2003/0097129 A1 | 5/2003 | Davison et al. |
| 2003/0099279 A1 | 5/2003 | Venkatasubramanian et al. |
| 2003/0109869 A1 | 6/2003 | Shadduck |
| 2003/0130655 A1 | 7/2003 | Woloszko et al. |
| 2003/0130738 A1 | 7/2003 | Hovda et al. |
| 2003/0144654 A1 | 7/2003 | Hilal |
| 2003/0158545 A1 | 8/2003 | Hovda et al. |
| 2003/0163178 A1 | 8/2003 | Davison et al. |
| 2003/0181922 A1 | 9/2003 | Alferness |
| 2003/0212394 A1 | 11/2003 | Pearson et al. |
| 2003/0212395 A1 | 11/2003 | Woloszko et al. |
| 2003/0225364 A1 | 12/2003 | Kraft et al. |
| 2004/0024398 A1 | 2/2004 | Hovda et al. |
| 2004/0024399 A1 | 2/2004 | Sharps et al. |
| 2004/0031494 A1 | 2/2004 | Danek et al. |
| 2004/0038868 A1 | 2/2004 | Ingenito |
| 2004/0047855 A1 | 3/2004 | Ingenito |
| 2004/0049180 A1 | 3/2004 | Sharps et al. |
| 2004/0054366 A1 | 3/2004 | Davison et al. |
| 2004/0055606 A1 | 3/2004 | Hendricksen et al. |
| 2004/0068256 A1 | 4/2004 | Rizoiu et al. |
| 2004/0068306 A1 | 4/2004 | Shadduck |
| 2004/0087937 A1 | 5/2004 | Eggers et al. |
| 2004/0116922 A1 | 6/2004 | Hovda et al. |
| 2004/0193150 A1 | 9/2004 | Sharkey et al. |
| 2004/0199226 A1 | 10/2004 | Shadduck |
| 2004/0230190 A1 | 11/2004 | Dahla et al. |
| 2004/0254532 A1 | 12/2004 | Mehier |
| 2005/0004634 A1 | 1/2005 | Ricart et al. |
| 2005/0010205 A1 | 1/2005 | Hovda et al. |
| 2005/0119650 A1 | 6/2005 | Sanders et al. |
| 2005/0166925 A1 | 8/2005 | Wilson et al. |
| 2005/0171582 A1 | 8/2005 | Matlock |
| 2005/0187543 A1 | 8/2005 | Underwood et al. |
| 2005/0215991 A1 | 9/2005 | Altman et al. |
| 2005/0222485 A1 | 10/2005 | Shaw et al. |
| 2005/0228423 A1 | 10/2005 | Khashayar et al. |
| 2005/0228424 A1 | 10/2005 | Khashayar et al. |
| 2005/0240171 A1 | 10/2005 | Forrest |
| 2005/0267468 A1 | 12/2005 | Truckai et al. |
| 2005/0283143 A1 | 12/2005 | Rizoiu |
| 2006/0004400 A1 | 1/2006 | McGurk et al. |
| 2006/0047291 A1 | 3/2006 | Barry |
| 2006/0085054 A1 | 4/2006 | Zikorus et al. |
| 2006/0100619 A1 | 5/2006 | McClurken et al. |
| 2006/0130830 A1 | 6/2006 | Barry |
| 2006/0135955 A1 | 6/2006 | Shadduck |
| 2006/0142783 A1 | 6/2006 | Lewis et al. |
| 2006/0161233 A1 | 7/2006 | Barry et al. |
| 2006/0200076 A1 | 9/2006 | Gonzalez et al. |
| 2006/0206150 A1 | 9/2006 | Demarais et al. |
| 2006/0224154 A1 | 10/2006 | Shadduck et al. |
| 2006/0271111 A1 | 11/2006 | Demarais et al. |
| 2007/0032785 A1 | 2/2007 | Diederich et al. |
| 2007/0036417 A1 | 2/2007 | Argiro et al. |
| 2007/0091087 A1 | 4/2007 | Zuiderveld |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0265687 A1 | 11/2007 | Deem et al. |
| 2008/0033493 A1 | 2/2008 | Deckman et al. |
| 2008/0103566 A1 | 5/2008 | Mehier |
| 2008/0110457 A1 | 5/2008 | Barry et al. |
| 2008/0114297 A1 | 5/2008 | Barry et al. |
| 2008/0125747 A1 | 5/2008 | Prokop |
| 2008/0132826 A1 | 6/2008 | Shadduck et al. |
| 2008/0213331 A1 | 9/2008 | Gelfand et al. |
| 2008/0255642 A1 | 10/2008 | Zarins et al. |
| 2009/0030412 A1 | 1/2009 | Willis et al. |
| 2009/0036948 A1 | 2/2009 | Levin et al. |
| 2009/0062873 A1 | 3/2009 | Wu et al. |
| 2009/0076409 A1 | 3/2009 | Wu et al. |
| 2009/0105702 A1 | 4/2009 | Shadduck |
| 2009/0105703 A1 | 4/2009 | Shadduck |
| 2009/0149846 A1 | 6/2009 | Hoey et al. |
| 2009/0216220 A1 | 8/2009 | Hoey et al. |
| 2009/0312753 A1 | 12/2009 | Shadduck |
| 2010/0076416 A1 | 3/2010 | Hoey et al. |
| 2010/0137860 A1 | 6/2010 | Demarais et al. |
| 2010/0137952 A1 | 6/2010 | Demarais et al. |
| 2010/0160905 A1 | 6/2010 | Shadduck |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0179528 A1 | 7/2010 | Shadduck et al. |

(56) References Cited

U.S. PATENT DOCUMENTS

| | | |
|---|---|---|
| 2010/0185189 A1 | 7/2010 | Hoey |
| 2010/0191112 A1 | 7/2010 | Demarais et al. |
| 2010/0204688 A1 | 8/2010 | Hoey et al. |
| 2010/0222851 A1 | 9/2010 | Deem et al. |
| 2010/0222854 A1 | 9/2010 | Demarais et al. |
| 2010/0249773 A1 | 9/2010 | Clark et al. |
| 2010/0262133 A1 | 10/2010 | Hoey et al. |
| 2010/0268307 A1 | 10/2010 | Demarais et al. |
| 2011/0060324 A1 | 3/2011 | Wu et al. |
| 2011/0077628 A1 | 3/2011 | Hoey et al. |
| 2011/0112400 A1 | 5/2011 | Emery et al. |
| 2011/0118717 A1 | 5/2011 | Shadduck |
| 2011/0160648 A1 | 6/2011 | Hoey |
| 2011/0166499 A1 | 7/2011 | Demarais et al. |
| 2011/0178570 A1 | 7/2011 | Demarais |
| 2011/0200171 A1 | 8/2011 | Beetel et al. |
| 2011/0202098 A1 | 8/2011 | Demarais et al. |
| 2011/0208096 A1 | 8/2011 | Demarais et al. |
| 2011/0257564 A1 | 10/2011 | Demarais et al. |
| 2011/0264011 A1 | 10/2011 | Wu et al. |
| 2011/0264075 A1 | 10/2011 | Leung et al. |
| 2011/0264090 A1 | 10/2011 | Shadduck et al. |
| 2012/0065632 A1 | 3/2012 | Shadduck |
| 2012/0101413 A1 | 4/2012 | Beetel et al. |
| 2012/0101538 A1 | 4/2012 | Ballakur et al. |
| 2012/0116382 A1 | 5/2012 | Ku et al. |
| 2012/0116383 A1 | 5/2012 | Mauch et al. |
| 2012/0116486 A1 | 5/2012 | Naga et al. |
| 2012/0130289 A1 | 5/2012 | Demarais et al. |
| 2012/0130345 A1 | 5/2012 | Levin et al. |
| 2012/0130359 A1 | 5/2012 | Turovskiy |
| 2012/0130360 A1 | 5/2012 | Buckley et al. |
| 2012/0130458 A1 | 5/2012 | Ryba et al. |
| 2012/0136344 A1 | 5/2012 | Buckley et al. |
| 2012/0136350 A1 | 5/2012 | Goshgarian et al. |
| 2012/0136417 A1 | 5/2012 | Buckley et al. |
| 2012/0136418 A1 | 5/2012 | Buckley et al. |
| 2012/0143181 A1 | 6/2012 | Demarais et al. |
| 2012/0143293 A1 | 6/2012 | Mauch et al. |
| 2012/0150267 A1 | 6/2012 | Buckley et al. |
| 2012/0158104 A1 | 6/2012 | Huynh et al. |
| 2012/0172837 A1 | 7/2012 | Demarais et al. |
| 2012/0197198 A1 | 8/2012 | Demarais et al. |
| 2012/0197252 A1 | 8/2012 | Deem et al. |
| 2013/0079772 A1 | 3/2013 | Shadduck |
| 2013/0116683 A1 | 5/2013 | Shadduck et al. |
| 2014/0018890 A1 | 1/2014 | Hoey et al. |
| 2014/0025057 A1 | 1/2014 | Hoey et al. |
| 2014/0031805 A1 | 1/2014 | Shadduck |

FOREIGN PATENT DOCUMENTS

| | | |
|---|---|---|
| WO | WO 02/069821 | 9/2002 |
| WO | WO 03/070302 | 8/2003 |
| WO | WO 03/086498 | 10/2003 |
| WO | WO 2005/025635 | 3/2005 |
| WO | WO 2005/102175 | 11/2005 |
| WO | WO 2006/003665 | 1/2006 |
| WO | WO 2006/055695 | 5/2006 |
| WO | WO 2009/009398 | 1/2009 |

OTHER PUBLICATIONS

Fishman et al., "A randomized trial comparing lung-volume-reduction surgery with medical therapy for severe emphysema," *N Engl J Med*, vol. 348, No. 21, pp. 2059-2073, May 22, 2003.

Homasson, et al., "Bronchoscopic cryotherapy for airway strictures caused by tumors," *Chest*, vol. 90, No. 2, pp. 159-164. Aug. 1986.

Li, K., "Efficient optimal net surface detection for image segmentation—from theory to practice," M.Sc. Thesis, The University of Iowa, 2003.

Marasso, et al., "Cryosurgery in bronchoscopic treatment of tracheobronchial stenosis," *Chest*, vol. 103, No. 2, pp. 472-474. Feb. 1993.

Marasso, et al., "Radiofrequency resection of bronchial tumours in combination with cryotherapy: evaluation of a new technique," *Thorax*, vol. 53, pp. 106-109, 1998.

Mathur et al., "Fiberoptic bronchoscopic cryotherapy in the management of tracheobronchial obstruction," *Chest*, vol. 110, No. 3, pp. 718-723, Sep. 1996.

Morice et al. "Endobrinchial argon plasma coagulation for treatment of hemotysis and neoplastic airway obstruction," *Chest*, vol. 119, No. 3 pp. 781-787, Mar. 2001.

Moulding et al., "Preliminary studies for achieving transcervical oviduct occlusion by hot water or low-pressure steam," *Advancesin Planned Parenthood*, vol. 12, No. 12; pp. 79-85, 1977.

Quin, J., "Use of neodymium yttrium aluminum garnet laser in long-term palliation of airway obstruction," *Connecticut Medicine*, vol. 59, No. 7, pp. 407-412, Jul. 1995.

Sutedja, et al., "Bronchoscopic treatment of lung tumors," *Elsevier, Lung Cancer*, 11, pp. 1-17, 1994.

Tschirren et al.; "Intrathoracic airway trees: segmentation and airway morphology analysis from low-dose CT scans;" *IEEE Trans. Med. Imaging*. vol. 24, No. 12; pp. 1529-1539, Dec. 2005.

Tschirren, J., "Segmentation, anatomical labeling, branchpoint matching, and quantitative analysis of human airway trees in volumetric CT images," Ph.D. Thesis, The University of Iowa, 231 pages, Aug. 2003.

Tschirren, J., "Segmentation, anatomical labeling, branchpoint matching, and quantitative analysis of human airway trees in volumetric CT images," Slides from Ph.D. defense, University of Iowa, 130 pages, Aug. 2003.

Unger, M. et al. "Monolithic Microfabricated Valves and Pumps by Multilayer Soft Lithography," *Science*, vol. 288, pp. 113-116, Apr. 7, 2000, accessed at http://web.mit.edu/thorsen/www/113.pdf.

Xia, Y. et al. "Soft Lithography," *Annu. Rev. Mater. Sci.*, vol. 28, pp. 153-184, 1998, accessed at http://www.bwfoundry.com/xia.pdf.

\* cited by examiner

MEDICAL INSTRUMENT AND METHOD OF USE

CROSS-REFERENCE TO RELATED APPLICATIONS

This application is a divisional of U.S. patent application Ser. No. 11/329,381 filed Jan. 10, 2006, now U.S. Pat. No. 8,444,636, which claims benefit of Provisional U.S. Patent Application Ser. No. 60/643,045 filed Jan. 11, 2005 titled Surgical Instrument and Method of Use. U.S. patent application Ser. No. 11/329,381 also is a continuation-in-part of U.S. application Ser. No. 10/681,625, filed Oct. 7, 2003 titled Medical Instruments and Techniques for Thermally-Mediated Therapies now U.S. Pat. No. 7,674,259, which is a continuation-in-part-of Ser. No. 10/017,582, filed on Dec. 7, 2001, titled Medical Instruments and Techniques for Highly Localized Thermally-Mediated Therapies now U.S. Pat. No. 6,669,694. U.S. patent application Ser. No. 11/329,381 also is a continuation-in-part of U.S. application Ser. No. 11/158,930 filed Jun. 22, 2005 titled Medical Instruments and Techniques for Treating Pulmonary Disorders now U.S. Pat. No. 7,892,229. U.S. patent application Ser. No. 11/329,381 also is a continuation-in-part of U.S. application Ser. No. 11/244,329 filed Oct. 5, 2005 titled Medical Instrument and Method of Use now U.S. Pat. No. 8,016,823. Provisional U.S. Patent Application Ser. No. 60/643,045 and U.S. application Ser. Nos. 10/681,625, 11/158,930, 11/244,329, and 11/329,381 are incorporated herein by this reference and made a part of this specification, together with the specifications of all other commonly-invented applications cited in the above applications.

FIELD OF THE INVENTION

This invention relates to surgical instruments for applying energy to tissue, and more particularly relates to a system for ablating, shrinking, sealing, welding, volumetrically removing or creating lesions in body structure or tissue by means of contacting body structure with non-ionized vapor phase media wherein a subsequent vapor-to-liquid phase change of the media applies thermal energy to the body structure.

BACKGROUND OF THE INVENTION

Various types of radiofrequency (Rf) and laser surgical instruments have been developed for delivering thermal energy to tissue, for example to cause hemostasis, to weld tissue or to ablate tissue. While such prior art forms of energy delivery work well for some applications, Rf and laser energy typically cannot cause highly "controlled" and "localized" thermal effects that are desirable in microsurgeries or other precision surgeries. In general, the non-linear or non-uniform characteristics of tissue affect both laser and Rf energy distributions in tissue.

What is needed is an instrument and method that can controllably deliver thermal energy to targeted tissues to ablate, coagulate, seal, shrink, or disintegrate tissue that does not cause stray electrical current flow in tissue.

SUMMARY OF THE INVENTION

The present invention is adapted to provide improved methods of controlled thermal energy delivery to localized tissue volumes, for example for ablating, sealing, coagulating or otherwise damaging the tissue. Of particular interest, the method causes thermal effects in targeted tissue without the use of RI current flow through the patient's body.

In general, the thermally-mediated treatment method comprises causing a vapor-to-liquid phase state change in a selected media at a targeted tissue site thereby applying thermal energy substantially equal to the heat of vaporization of the selected media to said tissue site. The thermally-mediated therapy can be delivered to tissue by such vapor-to-liquid phase transitions, or "internal energy" releases, about the working surfaces of several types of instruments for endoluminal treatments or for soft tissue thermotherapies. FIGS. 1A and 1B illustrate the phenomena of phase transitional releases of internal energies. Such internal energy involves energy on the molecular and atomic scale— and in polyatomic gases is directly related to intermolecular attractive forces, as well as rotational and vibrational kinetic energy. In other words, the method of the invention exploits the phenomenon of internal energy transitions between gaseous and liquid phases that involve very large amounts of energy compared to specific heat.

It has been found that the controlled application of internal energies in an introduced media-tissue interaction solves many of the vexing problems associated with energy-tissue interactions in Rf, laser and ultrasound modalities. The apparatus of the invention provides a fluid-carrying chamber in the interior of the device or working end. A source provides liquid media to the interior chamber wherein energy is applied to instantly vaporize the media. In the process of the liquid-to-vapor phase transition of a saline media in the interior of the working end, large amounts of energy are added to overcome the cohesive forces between molecules in the liquid, and an additional amount of energy is requires to expand the liquid 1000+ percent (P$\Delta$D) into a resulting vapor phase (see FIG. 1A). Conversely, in the vapor-to-liquid transition, such energy will be released at the phase transitions at the targeted tissue interface. That is, the heat of vaporization is released in tissue when the media transitioning from gaseous phase to liquid phase wherein the random, disordered motion of molecules in the vapor regain cohesion to convert to a liquid media. This release of energy (defined as the capacity for doing work) relating to intermolecular attractive forces is transformed into therapeutic heat form thermotherapy within a targeted body structure. Heat flow and work are both ways of transferring energy.

In FIG. 1A, the simplified visualization of internal energy is useful for understanding phase transition phenomena that involve internal energy transitions between liquid and vapor phases. If heat were added at a constant rate in FIG. 1A (graphically represented as 5 calories/gm blocks) to elevate the temperature of water through its phase change to a vapor phase, the additional energy required to achieve the phase change (latent heat of vaporization) is represented by the large number of 110+ blocks of energy at 100° C. Still referring to FIG. 1A, it can be easily understood that all other prior art ablation modalities—Rf, laser, microwave and ultrasound—create energy densities by simply ramping up calories/gm as indicated by the temperature range from 37° C. through 100° C. as in FIG. 1A. The prior art modalities make no use of the phenomenon of phase transition energies as depicted in FIG. 1A.

FIG. 1B graphically represents a block diagram relating to energy delivery aspects of the present invention. The system provides for insulative containment of an initial primary energy-media within an interior chamber of an instrument's working end. The initial, ascendant energy-media interaction delivers energy sufficient to achieve the heat of vaporization of a selected liquid media such as saline within an interior of the instrument body. This aspect of the technology requires an inventive energy source and controller—since energy application from the source to the selected media (Rf, laser, microwave etc.) must be modulated between very large energy densities to initially surpass the latent heat of vaporization of the media within milliseconds, and possible subsequent lesser energy densities for maintaining the media in its vapor phase. Additionally, the energy delivery system is coupled to a pressure control system for replenishing the selected liquid phase media at the required rate—and optionally for controlling propagation velocity of the vapor phase media from the working end surface of the instrument. In use, the method of the invention comprises the controlled deposition of a large amount of energy—the heat of vaporization as in FIG. 1A—when the vapor-to-liquid phase transition is controlled at the vapor media-tissue interface. The vapor-to-liquid phase transition deposits about 580 cal/gram within the targeted tissue site to perform the thermal ablation.

The systems and probes of the invention are configured for controlled application of the head of vaporization of a vapor-to liquid phase transition in an interface with tissue for tissue ablation, for the creation of lesions in tissue or volumetric removal of tissue. In general, the instrument and method of the invention cause thermal ablations rapidly and efficiently compared to conventional Rf energy delivery.

The instrument and method of the invention generate vapor phase media that is controllable as to volume and ejection pressure to provide a not-to-exceed temperature level that prevents desiccation, eschar, smoke and tissue sticking.

The instrument and method of the invention cause an energy-tissue interaction that is imageable with intra-operative ultrasound or MRI.

The instrument and method of the invention cause thermal effects in tissue that do not rely applying an electrical field across the tissue to be treated.

The instrument and method of the invention cause a liquid-to-vapor phase transition in an interior chamber of the device that utilizes negative temperature coefficient materials for modulating heating of saline inflows between (i) conducting heat to the saline media from a resistively heated component, and (ii) internal $I^2R$ heating of the saline inflows.

In one embodiment, the instrument and method include means for applying the heat of ionization to a non-ionized flow media to create a plasma at the working end for contacting tissue to thereby ablate the tissue.

Additional advantages of the invention will be apparent from the following description, the accompanying drawings and the appended claims.

DETAILED DESCRIPTION OF THE INVENTION

1. Type "A" Thermotherapy Instrument.

Figure 1A:
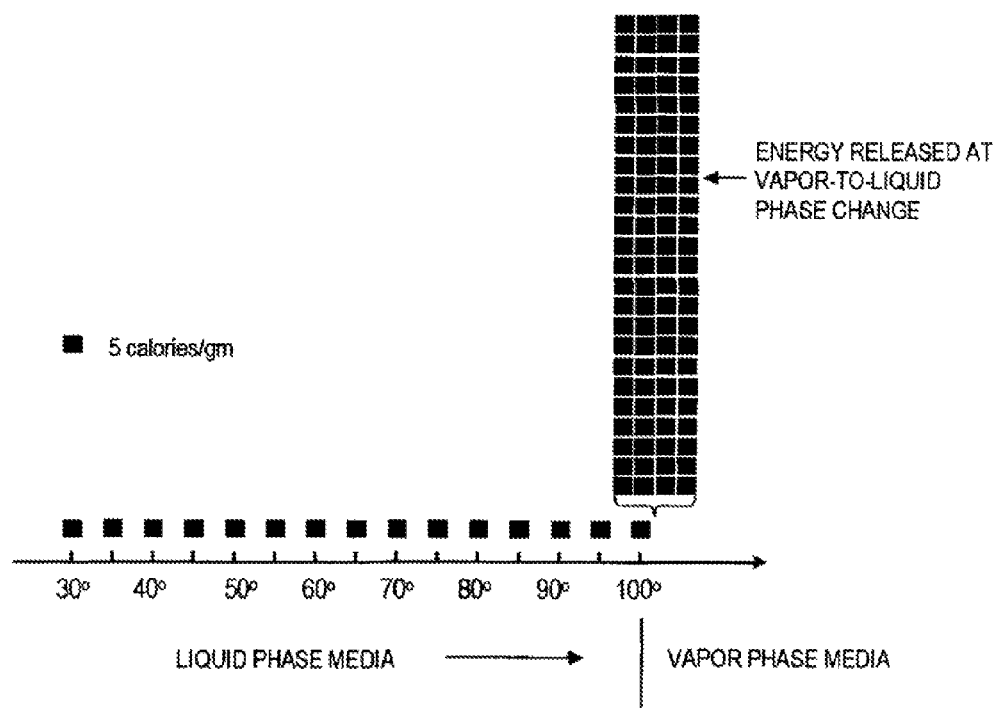
FIG. 1A is a graphical depiction of the quantity of energy needed to achieve the heat of vaporization of water.
Figure 1B:
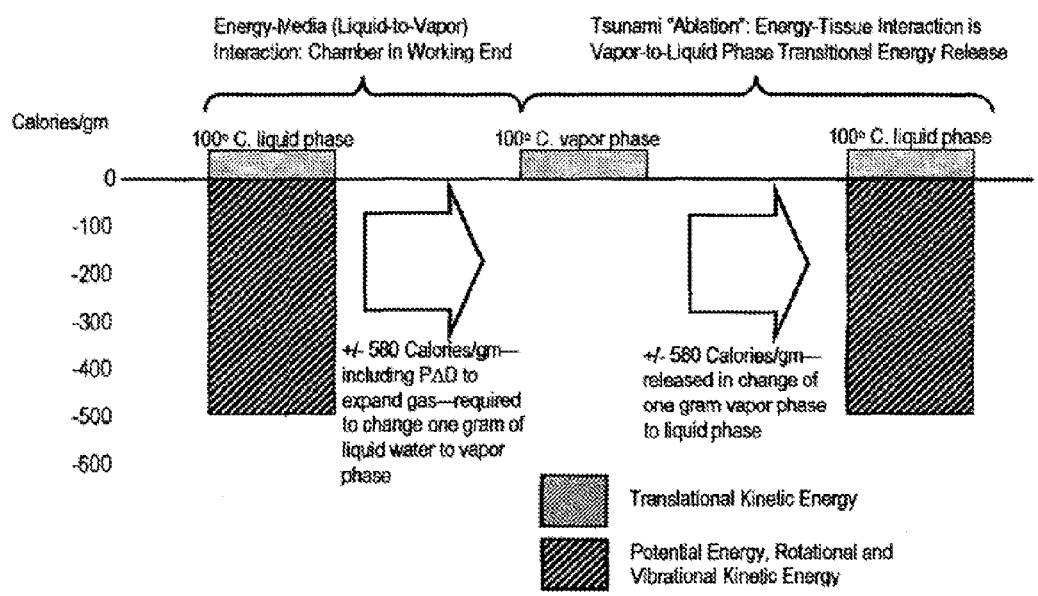
FIG. 1B is a diagram of phase change energy release that underlies one method of the invention.
Figure 2A:
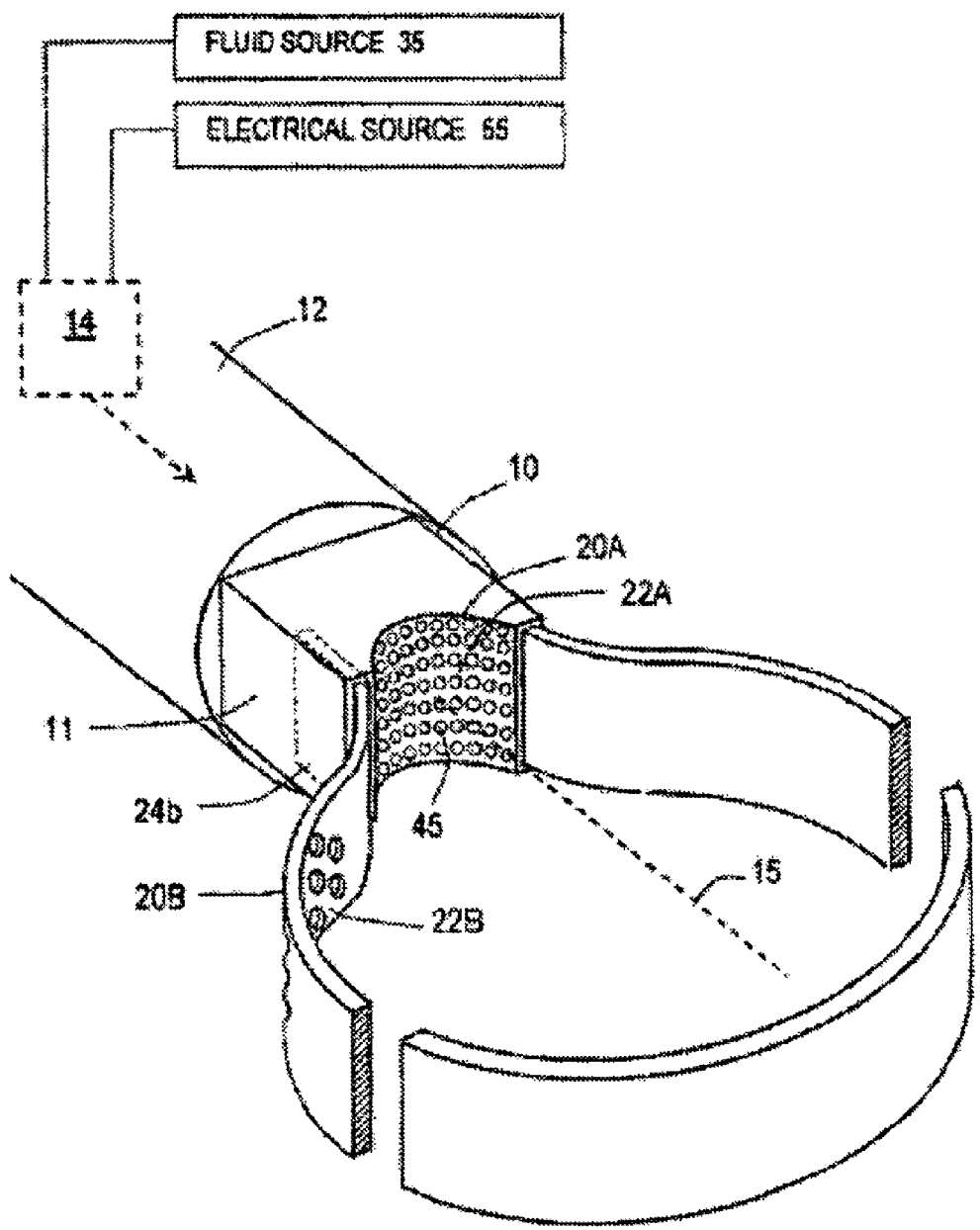
FIG. 2A is a perspective view of the working end of an exemplary Type "A" probe of the present invention with an openable-closeable tissue engaging structure in a first open position.
Figure 2B:
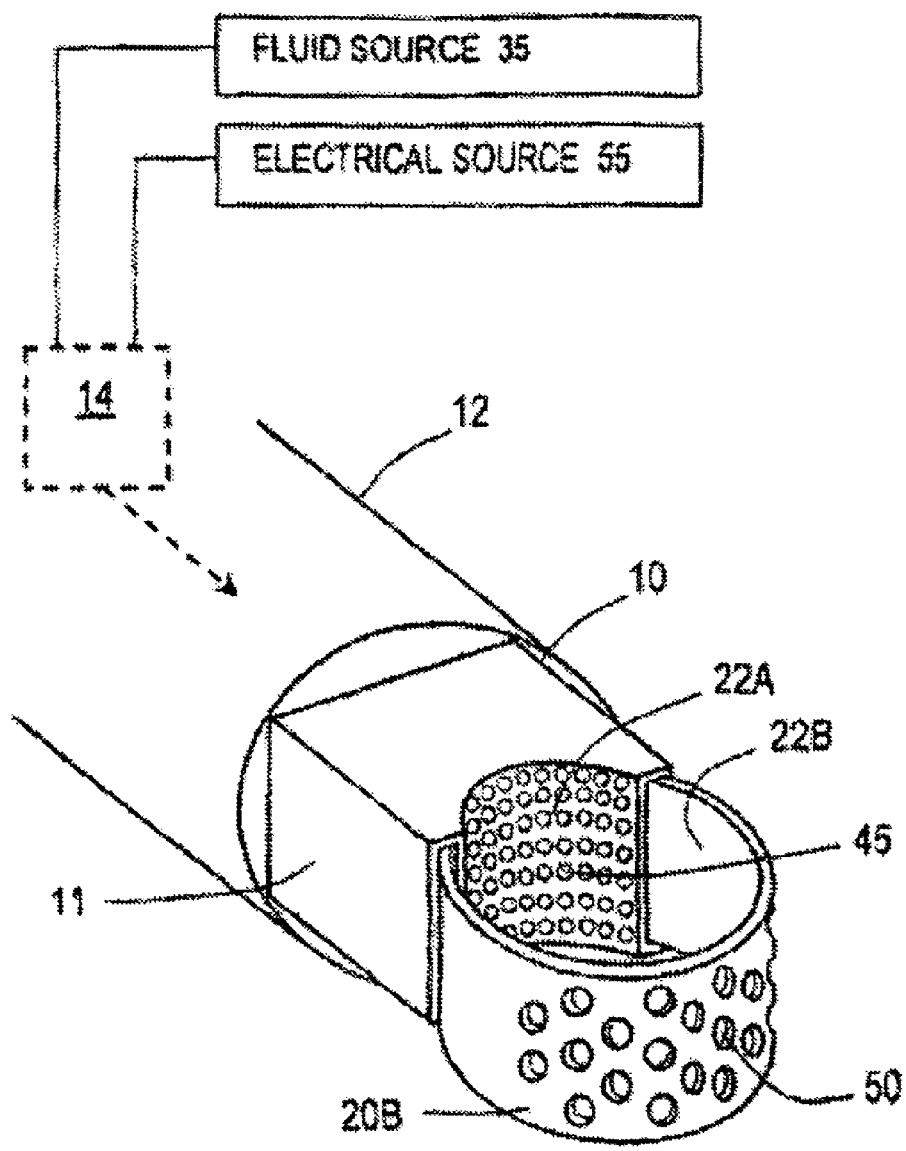
FIG. 2B is a perspective view similar to FIG. 2A probe of the present invention in a second closed position.
Figure 3:
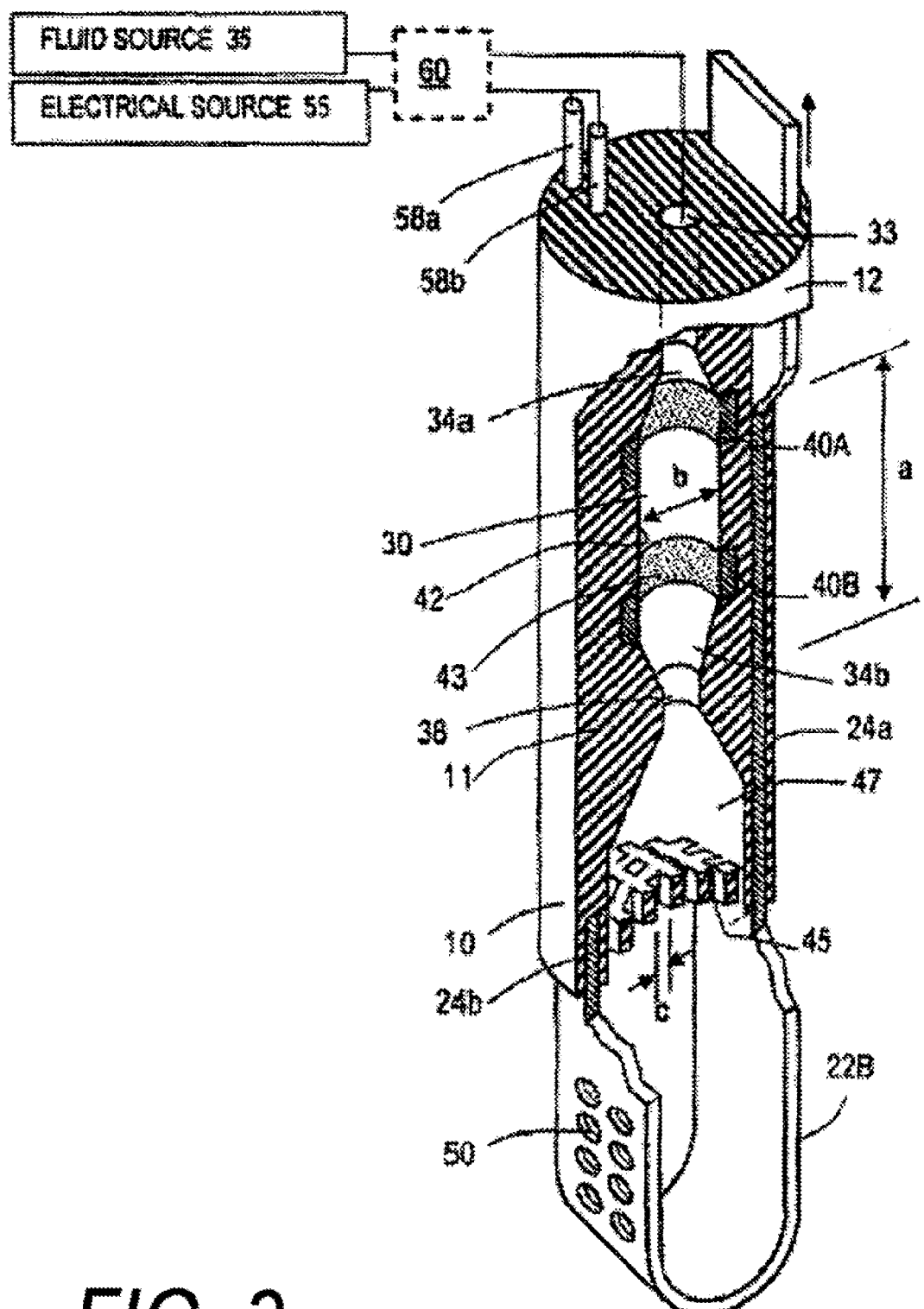
FIG. 3 is a cut-away view of the working end of FIGS. 2A-2B.

Referring to FIGS. 2A, 2B and 3, the working end 10 of a "A" system 5 of the present invention is shown that is adapted for endoscopic procedures in which a tissue volume T targeted for treatment (a thermoplasty) can be captured by a loop structure. The working end 10 comprises a body 11 of insulator material (see FIG. 3) coupled to the distal end of introducer member 12 extending along axis 15. In this exemplary embodiment, the working end 10 has a generally cylindrical cross-section and is made of any suitable material such as plastic, ceramic, glass, metal or a combination thereof. The working end 10 is substantially small in diameter (e.g., 2 mm to 5 mm) and in this embodiment is coupled to an elongate flexible introducer member 12 to cooperate with a working channel in an endoscope. Alternatively, the waking end 10 may be coupled to a rigid shall member having a suitable 1 mm to 5 mm or larger diameter to cooperate with a trocar sleeve for use in endoscopic or microsurgical procedures. A proximal handle portion 14 of the instrument indicated by the block diagram of FIG. 2A carries the various actuator mechanisms known in the art for actuating components of the instrument.

In FIGS. 2A, 2B and 3, it can be seen that the working end 10 carries an openable and closeable structure for capturing tissue between a first tissue-engaging surface 20A and a second tissue-engaging surface 20B. In this exemplary embodiment, the working end 10 and first tissue-engaging surface 20A comprises at non-moving component indicated at 22A that is defined by the exposed distal end of body 11 of working end 10. The second tissue-engaging surface 20B is carried in a moving component that comprises a flexible loop structure indicated at 22B.

The second moving component or flexible loop 22B is actuatable by a slidable portion 24a of the loop that extends through a slot 25 in the working end to an actuator in the handle portion 14 as is known in the art (see FIG. 3). The other end 24b of the loop structure 22B is fixed in body 11. While such an in-line (or axial) flexible slidable member is preferred as the tissue-capturing mechanism for a small diameter flexible catheter-type instrument, it should be appreciated that any openable and closable jaw structure known in the art falls within the scope of the invention, including forms of paired jaws with cam-surface actuation or conventional pin-type hinges and actuator mechanisms. FIG. 2A illustrates the first and second tissue-engaging surfaces 20A and 20B in a first spaced apart or open position. FIG. 2B shows the first and second surfaces 20A and 20B moved toward a second closed position.

Now turning to the fluid-to-gas energy delivery means of the invention, referring to FIG. 3, it can be seen that the insulated or non-conductive body 11 of working end 10 carries an interior chamber indicated at 30 communicating with lumen 33 that are together adapted for delivery and transient confinement of a fluid media M that flows into chamber 30. The chamber 30 communicates via lumen 33 with a fluid media source 35 that may be remote from the device, or a fluid reservoir (coupled to a remote pressure source) carried within introducer 12 or carried within a handle portion 14. The term fluid or flowable media source 35 is defined to include a positive pressure inflow system which preferably is any suitable high pressure pump means known in the art. The fluid delivery lumen 33 transitions to chamber 30 at proximal end portion 34a thereof. The distal end portion 34b of chamber 30 has a reduced cross-section that functions to direct vapor media through a small outlet or nozzle indicated at 38.

Of particular interest, still referring to FIG. 3, paired spaced apart electrode elements 40A and 40B are exposed in surface 42 of interior fluid confinement chamber 30. In this exemplary embodiment, the electrode elements 40A and 40B comprise circumferential exposed surfaces of a conductive material positioned at opposing proximal and distal ends of interior chamber 30, but other arrangements are possible. The invention can utilize any suitable configuration of spaced apart electrodes (e.g., such as concentric electrode surfaces, intertwined helical electrode surfaces, adjustable spaced apart surfaces, or porous electrodes) about at least one confinement chamber 30 or lumen portion of the system. Alternatively, each electrode can comprise one or more projecting elements that project into the chamber. The exemplary embodiment of FIG. 3 shows an elongate chamber having an axial dimension indicated at A and diameter or cross-section indicated at B. The axial dimension may range from about 0.1 mm to 20.0 mm and may be singular or plural as described below. The diameter B may range from micron dimensions (e.g., 0.5 µm) for miniaturized instruments to a larger dimension (e.g., 5.0 mm) for larger instruments for causing the thermally induced liquid-to-vapor transformation required to enable the novel phase change energy-tissue interaction of the invention. The electrodes are of any suitable material such as stainless steel, aluminum, nickel titanium platinum, gold, or copper. Each electrode surface preferably has a toothed surface texture indicated at 43 that includes hatching, projecting elements or surface asperities for better delivering high energy densities in the fluid proximate to the electrode. The electrical current to the working end 10 may be switched on and off by a foot pedal or any other suitable means such as a switch in handle 14.

FIG. 3 further shows that a preferred shape is formed into the tissue-engaging surface 20A to better perform the method of fusing tissue. As can be seen in FIGS. 2B and 3, the first tissue-engaging surface 20A is generally concave so as to be adapted to receive a greater tissue volume in the central portion of surface 20A. The second tissue-engaging surface 20B is flexible and naturally will be concave in the distal or opposite direction when tissue is engaged between surfaces 20A and 20B. This preferred shape structure allows for controllable compression of the thick targeted tissue volumes T centrally exposed to the energy delivery means and helps prevent conductance of thermal effects to collateral tissue regions CT (see FIG. 4) and as will be described in greater detail below.

FIGS. 2A and 3 show that first tissue-engaging surface 20A defines an open structure of at least one aperture or passageway indicated at 45 that allows vapor to pass therethrough. The apertures 45 may have any cross-sectional shape and linear or angular route through surface 20A with a sectional dimension C in this embodiment ranging upwards from micron dimensions (e.g., 0.5 µm) to about 2.0 mm in a large surface 20A. The exemplary embodiment of FIG. 3 has an expanding cross-section transition chamber 47 proximate to the aperture grid that transitions between the distal end 34b of chamber 30 and the apertures 45. However, it should be appreciated that such a transition chamber 47 is optional and the terminal portion of chamber 30 may directly exit into a plurality of passageways that each communicate with an aperture 45 in the grid of the first engaging surface 20A. In a preferred embodiment, the second tissue-engaging surface 20B defines (optionally) a grid of apertures indicated at 50 that pass through the loop 22B. These apertures 50 may be any suitable dimension (cf. apertures 45) and are adapted to generally oppose the first tissue-engaging surface 20A when the surfaces 20A and 20B are in the second closed position, as shown in FIG. 2B.

The electrodes 40A and 40B of working end 10 have opposing polarities and are coupled to Rf generator or electrical source 55. FIG. 3 shows current-carrying wire leads 58a and 58b that are coupled to electrodes 40A and 40B and extend to electrical source 55 and controller 60. In a preferred embodiment of the invention, either tissue-engaging surface optionally includes a sensor 62 (or sensor array) that is in contact with the targeted tissue surface (see FIG. 2A). Such a sensor, for example a thermocouple known in the art, can measure temperature at the surface of the captured tissue. The sensor is coupled to controller 60 by a lead (not shown) and can be used to modulate or terminate power delivery as will be described neat in the method of the invention.

Figure 4:
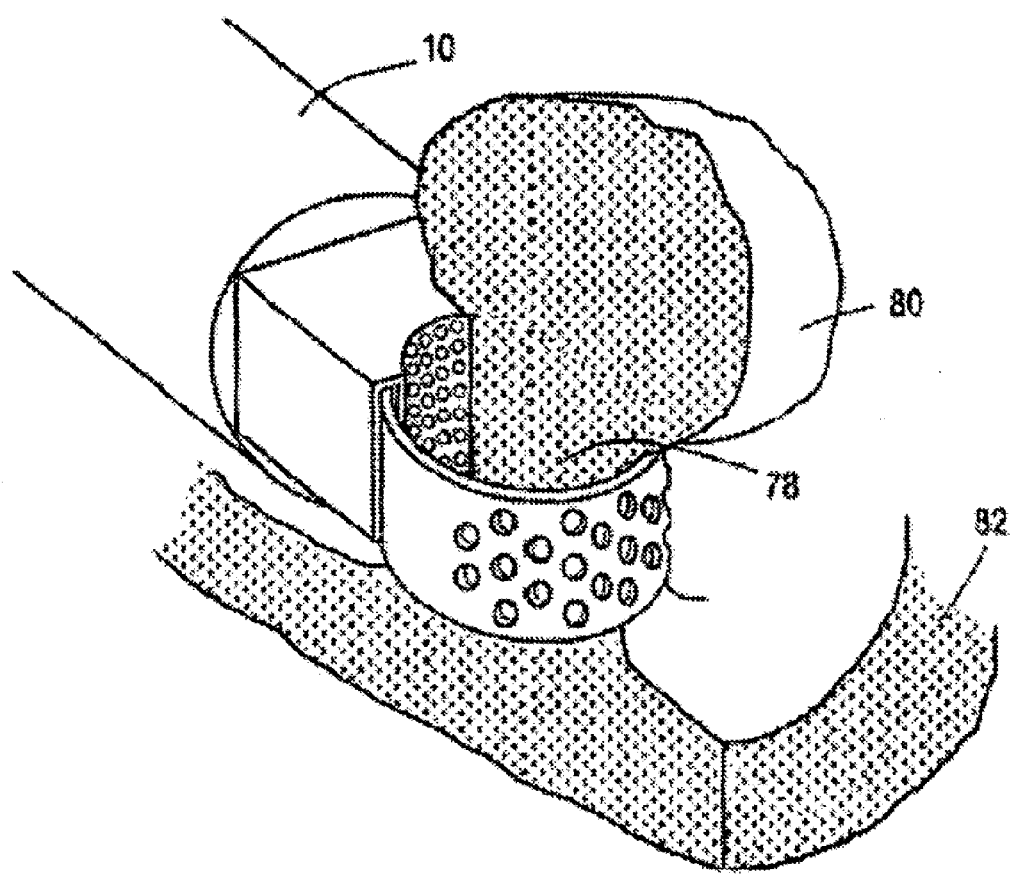
FIG. 4 is a perspective view of the working end of FIG. 3 capturing an exemplary tissue volume.

Operation and use of the working end of FIGS. 2A, 2B and 3 in performing a method of treating tissue can be briefly described as follows, for example in an endoscopic polyp removal procedure. As can be understood from FIG. 4, the working end 10 is carried by an elongate catheter-type member 12 that is introduced through a working channel 70 of an endoscope 72 to a working space. In this case, the tissue T targeted for sealing is a medial portion 78 of as polyp 80 in a colon 82. It can be easily understood that the slidable movement of the loop member 22B can capture the polyp 80 in the device as shown in FIG. 4 after being lassoed. The objective of the tissue treatment is to seal the medial portion of the polyp with the inventive thermotherapy. Thereafter, utilize a separate cutting instrument is used to cut through the sealed portion, and the excised polyp is retrieved for biopsy purposes.

Figure 5:
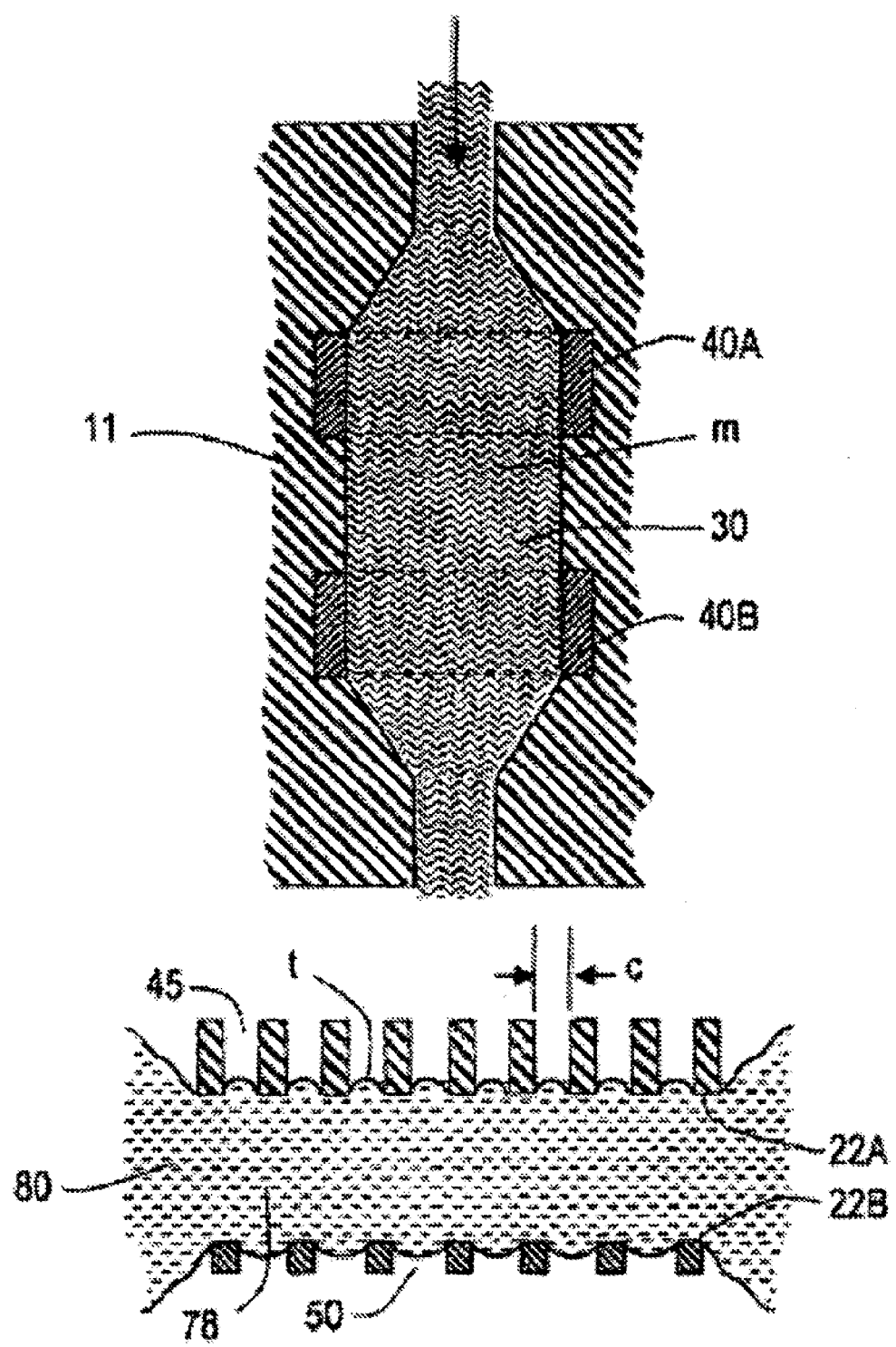
FIGS. 5-6 are sectional schematic views of working end of FIG. 3 depicting, in sequence, the steps of a method of the present invention to seal or weld a targeted tissue volume, FIG. 5 illustrating the pressurized delivery of a liquid media to an interior channel, and FIG. 6 depicting an electrical discharge that causes a liquid-to-gas phase change as well as the ejection of the vapor media into the targeted tissue to thermally seal engaged tissue.
Figure 6:
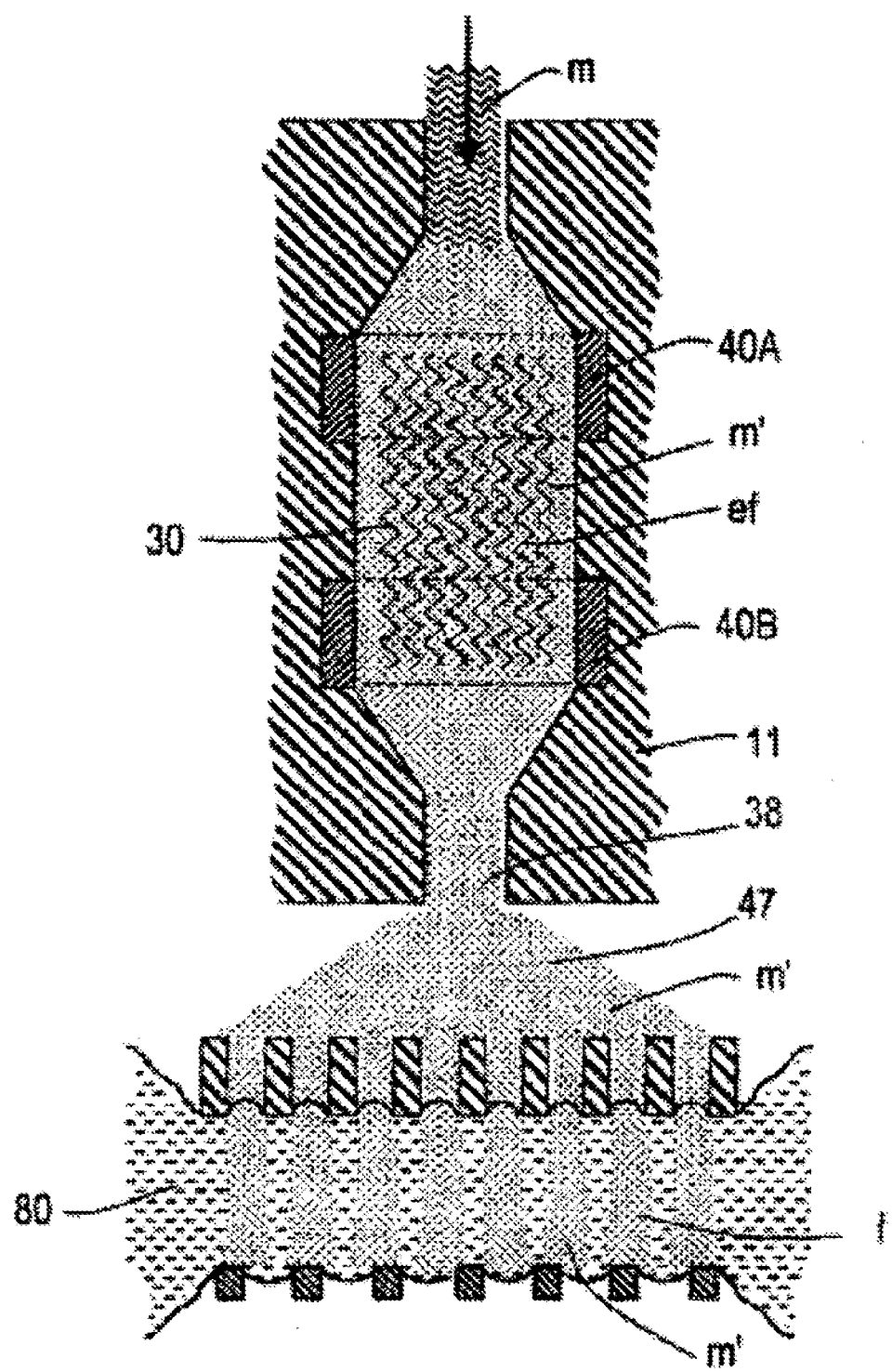

Now turning to FIGS. 5 and 6, two sequential schematic views of the working end engaging tissue T are provided to illustrate the energy-tissue interaction caused by the method of the invention. FIG. 5 depicts an initial step of the method wherein the operator sends a signal to the controller 60 to delivery fluid media M (e.g., saline solution or sterile water) through lumen 33 into chamber 30. FIG. 6 depicts the next step of the method wherein the controller delivers an intense discharge of electrical energy to the paired electrode elements 40A and 40B within chamber 30 indicated by electric field EF. The electrical discharge provides energy exceeding the heat of vaporization of the contained fluid volume. The explosive vaporization of fluid media M (of FIG. 5) into a vapor or gas media is indicated at M' in FIG. 6. The greatly increased volume of gas media M' results in the gas ejected from chamber 30 at high velocity through apertures 45 of surface 20A into the targeted tissue T. The liquid-to-vapor transition caused by the electrical discharge results in the vapor media M' having a temperature of 100° C. or more as well as carrying the heat of vaporization to deliver thermal effects into or through the targeted tissue T, as indicated graphically by the shaded regions of gas flow in FIG. 6. The fluid source and its pressure mechanism can provide any desired level of vapor ejection pressure. Depending on the character of the introduced liquid media, the media is altered from a first lesser temperature to a second greater temperature in the range of 100° C. or higher depending on pressure. The ejection of non-ionized vapor media M' and its condensation will uniformly and very rapidly elevate the temperature of the engaged tissue to the desired range of about 65° C. to 100° C. to cause hydrothermal denaturation of proteins in the tissue, and to cause optimal fluid inter-mixing of tissue constituents that will result in an effective seal. In effect, the vapor-to-liquid phase transition of the ejected media M' will deposit heat equal to the heat of vaporization (also sometimes called the heat of condensation) in the tissue. At the same time as the heat of vaporization of vapor media M' is absorbed by water in the targeted tissue, the media converts back to a liquid thus hydrating the targeted tissue T. Such protein denaturation by hydrothermal effects differentiates this method of tissue sealing or fusion from all other forms of energy delivery, such as radiofrequency energy delivery. All other forms of energy delivery vaporize intra- and extracellular fluids and cause tissue desiccation, dehydration or charring which is undesirable for the intermixing of denatured tissue constituents into a proteinaceous amalgam.

The above electrical energy deliver step is continuous or can be repeated at a high repetition rate to cause a pulsed form of thermal energy delivery in the engaged tissue. The fluid media M inflow may be continuous or pulsed to substantially fill chamber 30 before an electrical discharge is caused therein. The repetition rate of electrical discharges may be from about 1 Hz to 1000 Hz. More preferably, the repetition rate is from about 10 Hz to 200 Hz. The selected repetition rate preferably provides an interval between electrical discharges that allows for thermal relaxation of tissue, that may range from about 10 ms to 500 ms. The electrical source or voltage source 55 may provide a voltage ranging between about 20 volts and 10,000 volts to cause instant vaporization of the volume of fluid media M captured between the electrode elements 40A and 40B. After a selected time interval of such energy application to tissue T, that may range from about 1 second to 30 seconds, and preferably from about 5 to 20 seconds, the engaged tissue will be contain a core region in which the tissue constituents are denatured and intermixed under relatively high compression between surfaces 20A and 20B. Upon disengagement and cooling of the targeted tissue T, the treated tissue will be fused or welded. Over time, the body's wound healing response will reconstitute the treated tissue by means of fibrosis to create a collagenous volume or scar-like tissue.

2. Type "B" Thermotherapy Instrument.

Now referring to FIGS. 7-11, other embodiments of medical probes and vapor generation and delivery systems are shown. In the previous embodiment, the working end was optimized for engaging and sealing tissue with a working surface that is configured for clamped contact with tissue. In the embodiments of FIGS. 7-11, the probes and working ends are adapted for controlled application of energy by means of a vapor-to-liquid phase change energy release in an endoluminal application or in an interstitial application of energy.

Figure 7:
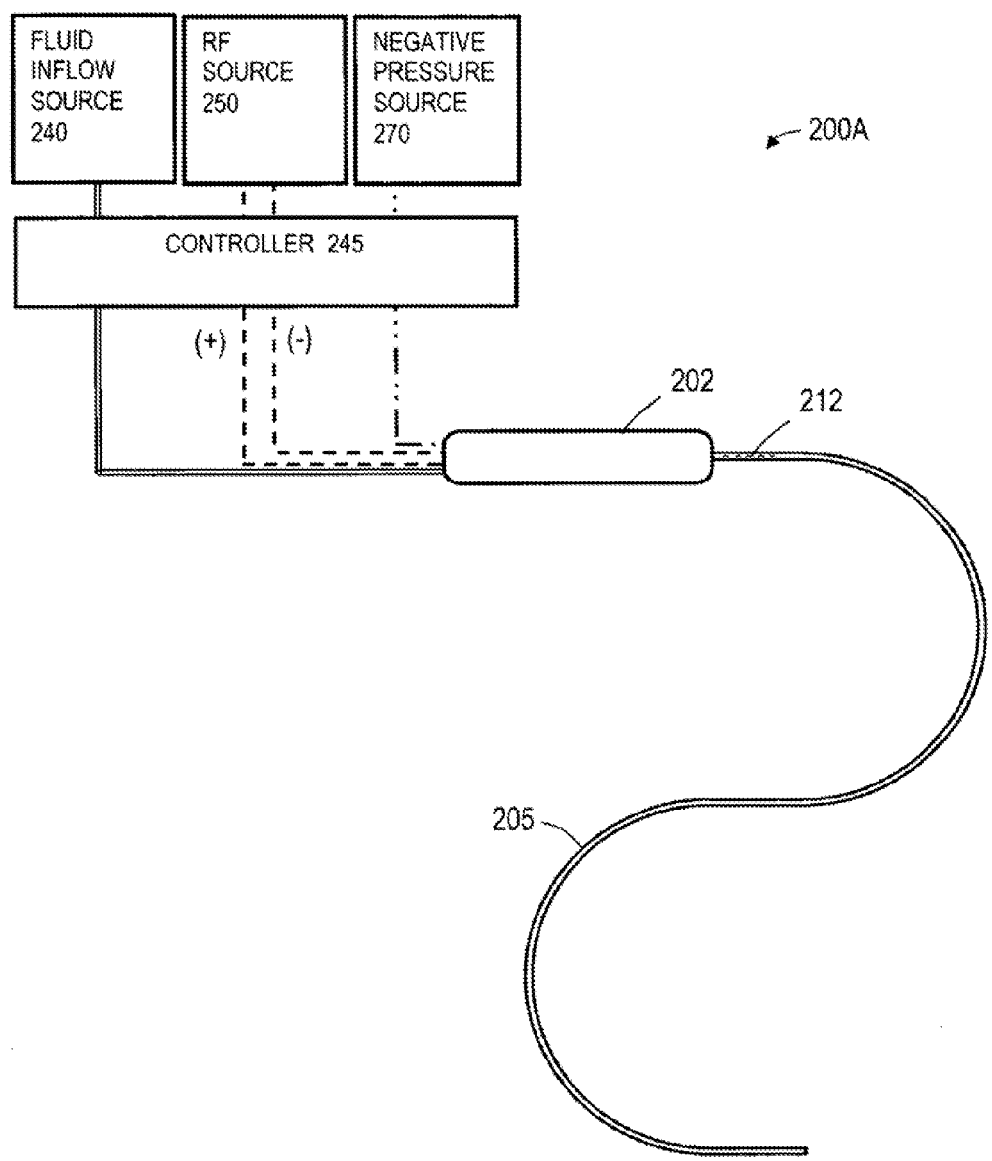
FIG. 7 is a Type "B" probe and system of present invention comprising a handle with internal energy delivery mechanism for providing a non-ionized vapor and an elongate extension member configured as a flexible catheter.

In FIG. 7, it can be seen that probe system 200A includes a handle portion 202 that transitions into an elongated extension member 205. In the embodiment of FIG. 7, the extension member 205 comprises a flexible catheter sleeve that is configured for introduction through a body lumen or cavity such as a blood vessel, a patient's airways, a sinus, a uterus, a fallopian tube or the like. The diameter of extension member 205 can range from about 1 Fr. to 6 Fr. or more. The fluid inflow source, energy delivery source and optional negative pressure source are operatively connected to handle portion 202 and are further described below.

Figure 8A:
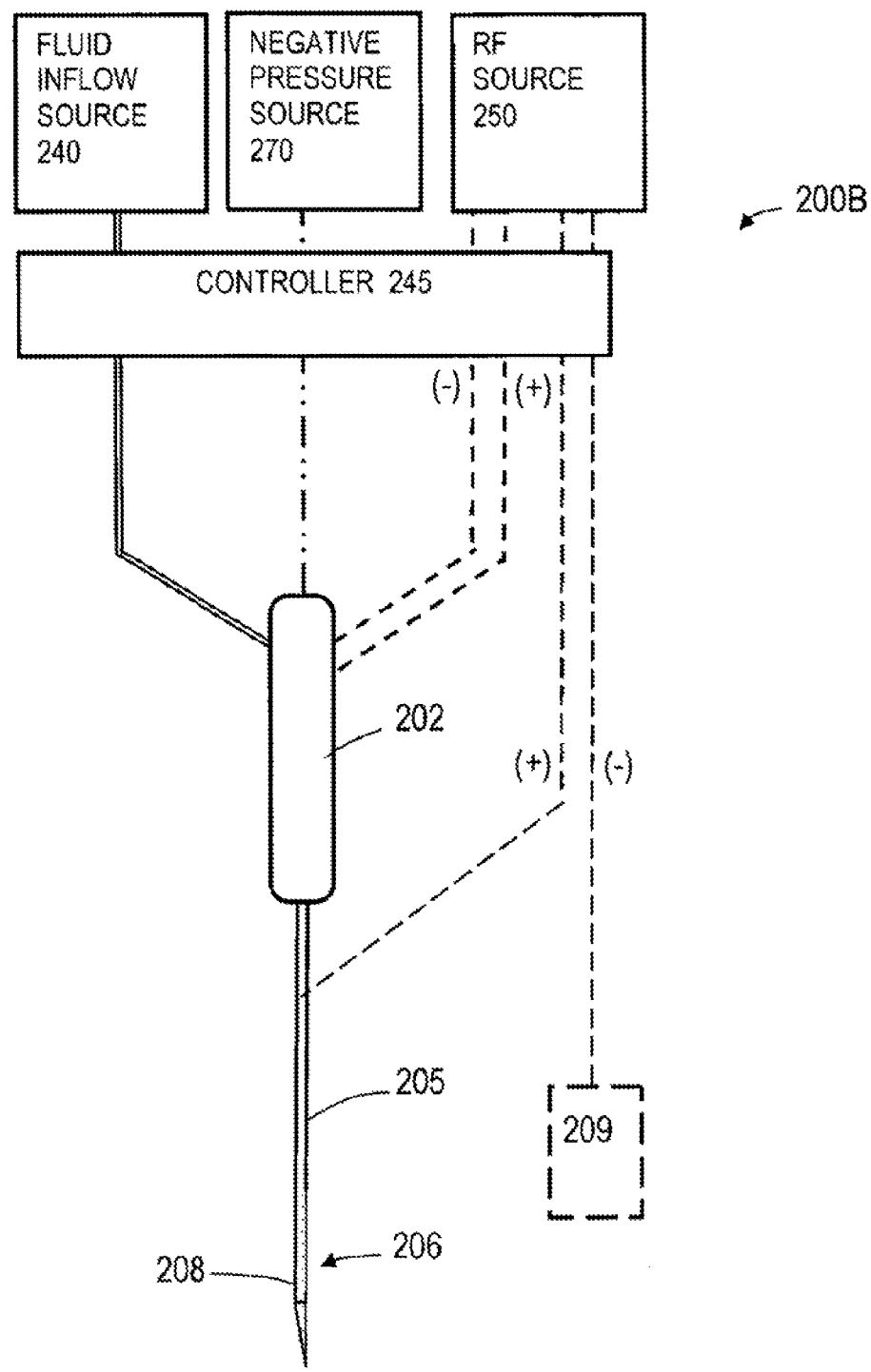
FIG. 8A is an alternative probe similar to the embodiment of FIG. 7 with an extension member configured with a rigid needle-like working end.
Figure 8B:
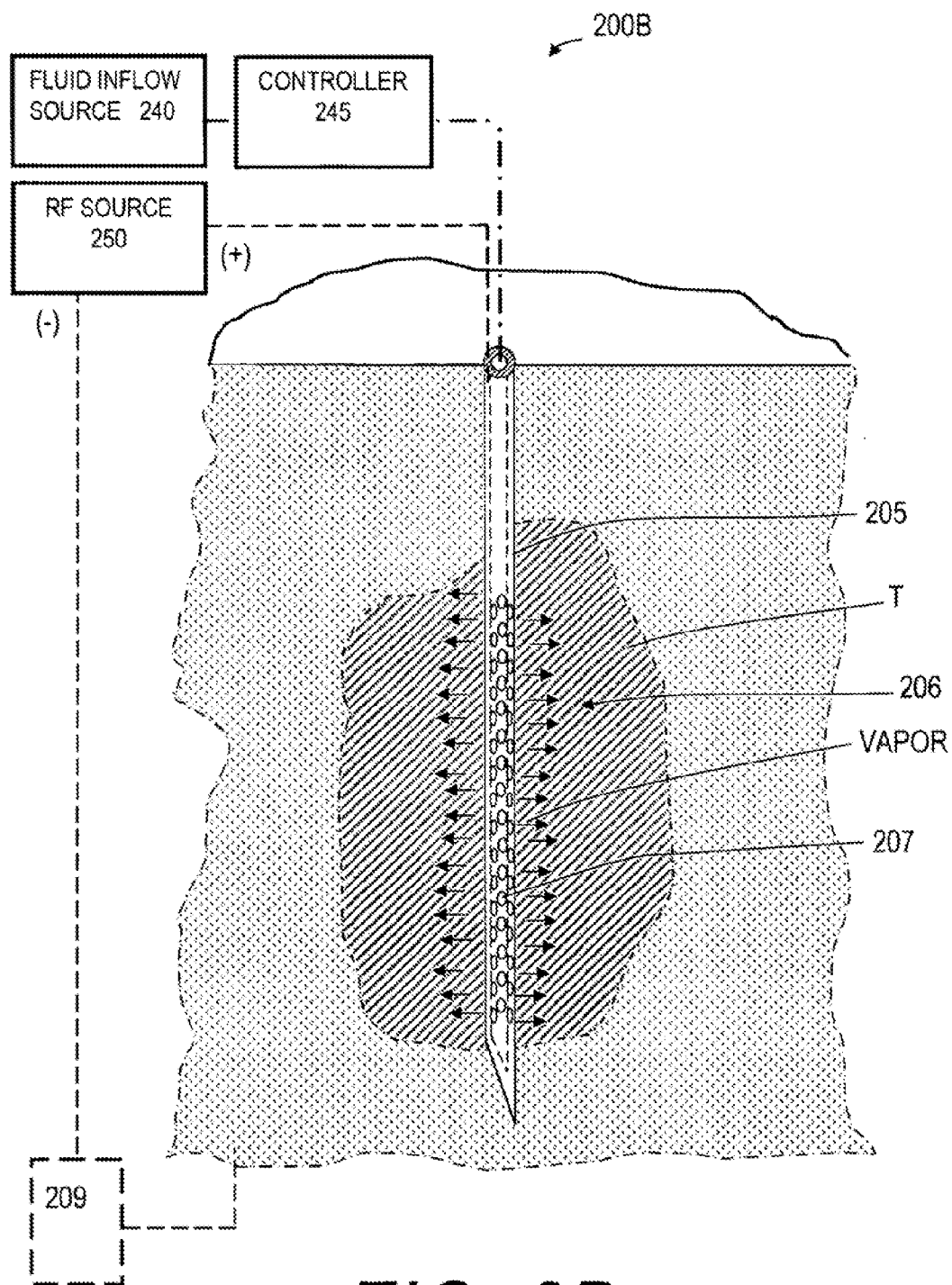
FIG. 8B is an illustration of the needle-like working end of FIG. 8A disposed in tissue showing a method of use in ablating a tumor.

In FIG. 8A, the probe system 200B consists of handle portion 202 that transitions into elongated extension member 205 that is substantially rigid and has a sharp hollow needle tip 206 for penetrating into tissue. FIG. 8B illustrates the needle tip 206 having a plurality of vapor ports or outlets 207 therein for the interstitial introduction of vapor. In one embodiment as in FIG. 8B, the probe 200B with a rigid needle-like working end can be configured with a cross-section and length suited for ablating a tumor in a liver, breast, lung, kidney, prostate, uterine wall or the like in an open or endoscopic approach. The fluid inflow source and energy delivery source are provided in handle portion 202 and are described in more detail below. In the probe embodiment 200B of FIGS. 8A-8B, the working end 206 also can comprise at least one electrode 208 for delivering high frequency energy to the tissue and/or the nor-ionized vapor media being introduced into targeted tissue T such as a tumor via the outlets 207 in the needle tip. FIGS. 8A-8B illustrate an electrode 208 in the needle tip cooperating with a ground pad 209.

Figure 9A:
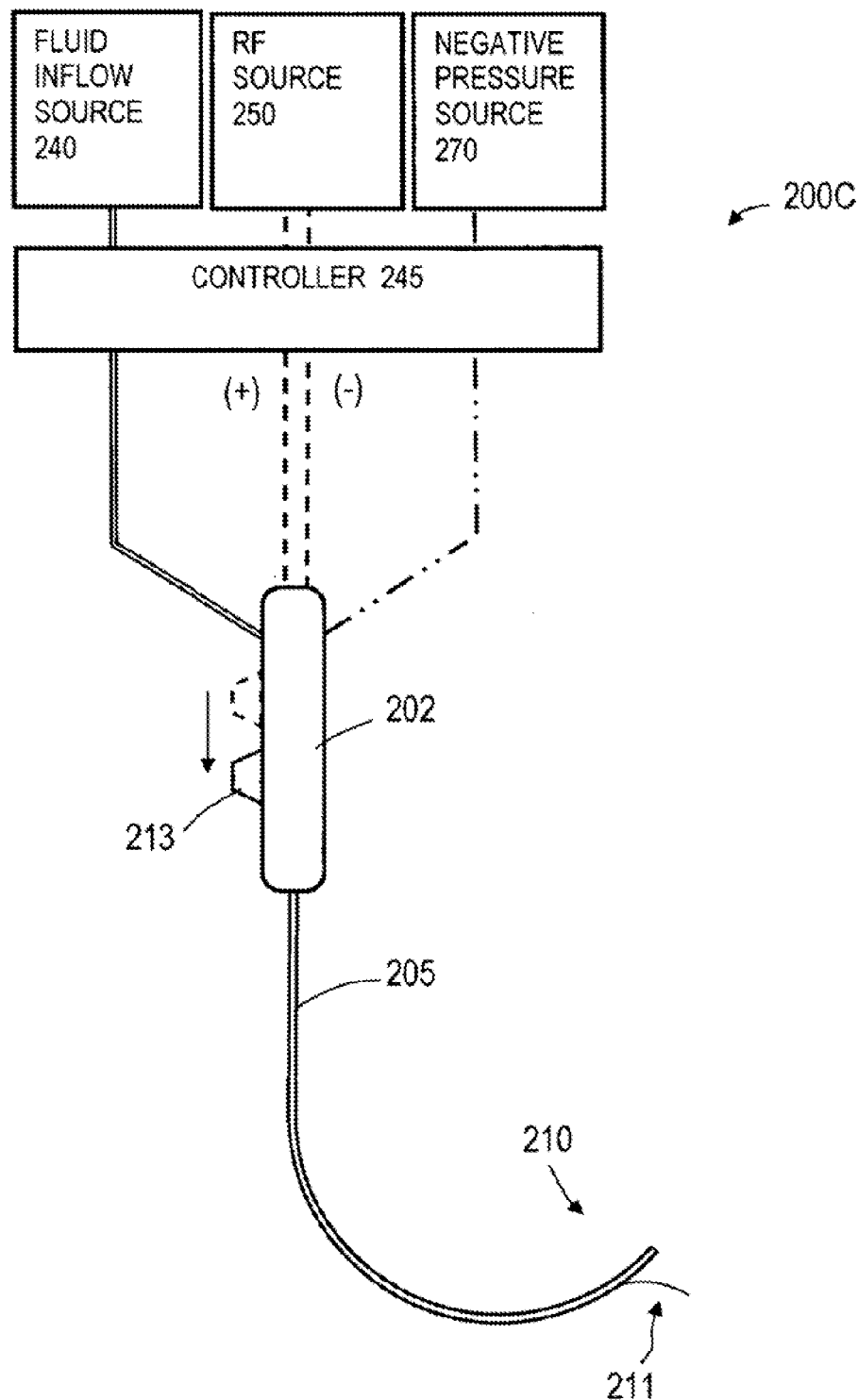
FIG. 9A is an alternative probe similar to the embodiment of FIG. 7 with an extension member configured as a flexible catheter with at least one hollow shape-memory needle extendable therefrom.
Figure 9B:
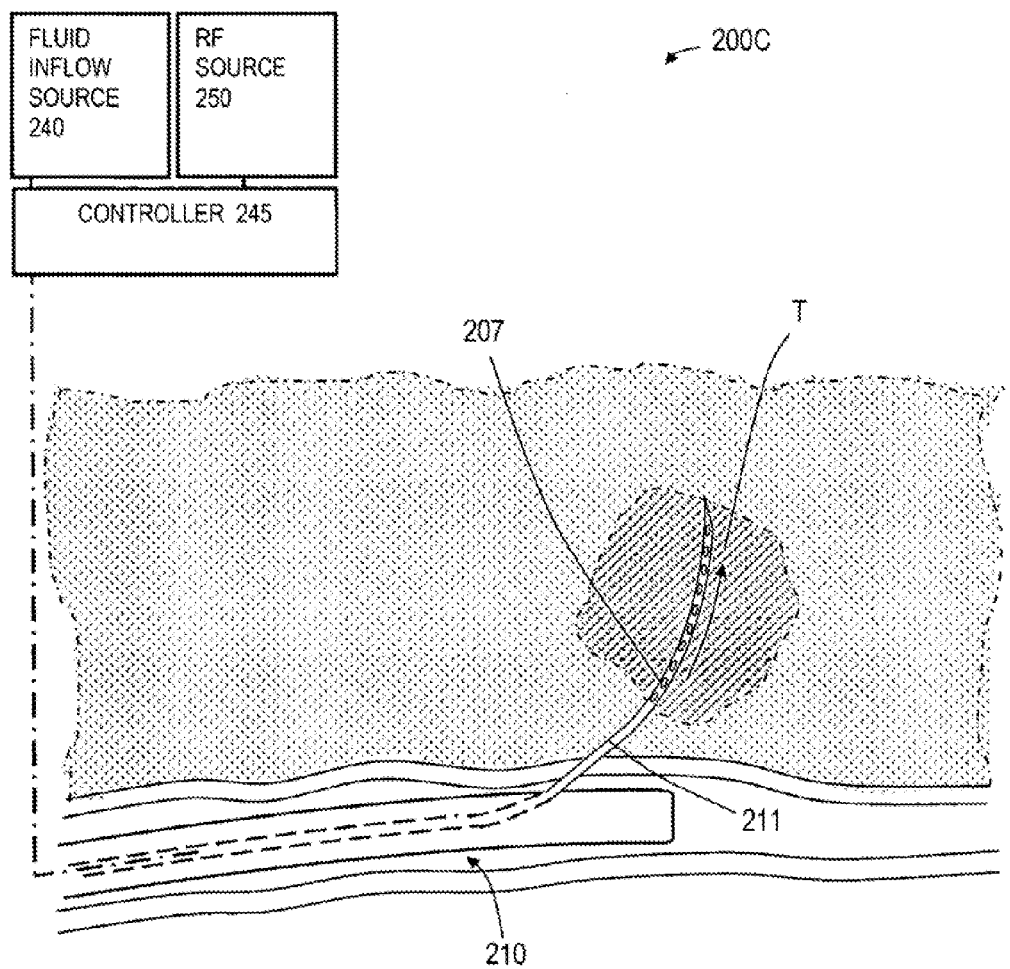
FIG. 9B is an illustration of a method of using the extendable needle of FIG. 9A to deliver energy to targeted tissue outside a body lumen such as a fibroid or lung tumor.

FIG. 9A-9B illustrate another the probe and system 200C that consists of handle portion 202 that transitions into an elongated member 205 that comprises a flexible catheter sleeve as in FIG. 7 with a working end 210 that carries at least one extendable-retractable hollow needle 211 for delivering vapor to treat tissue. The flexible elongated member 205 thus can be navigated through a body lumen and then the at least one needle 211 with vapor outlets 207 can be penetrated into tissue from the working, end as shown in FIG. 9B. The at least one needle 211 can be actuated by means of art actuator 213 in handle portion 202. An embodiment as in FIGS. 9A-9B can be configured with a cross-section and length for treating abnormal prostate tissue, abnormal uterine wall tissue, abnormal lung tissue, abnormal bladder tissue, abnormal gastrointestinal tract tissue and the like indicated at T. The working end 210 can further carry at least one balloon for stabilizing the working end in a body lumen or expanding in a body cavity to correctly localize the needle(s). The working end 210 can further carry an ultrasound transducer for imaging the treatment. The working end 210 can further include an aspiration channel coupled to a negative pressure source 270 for suctioning the lumen wall against the working end.

Figure 10:
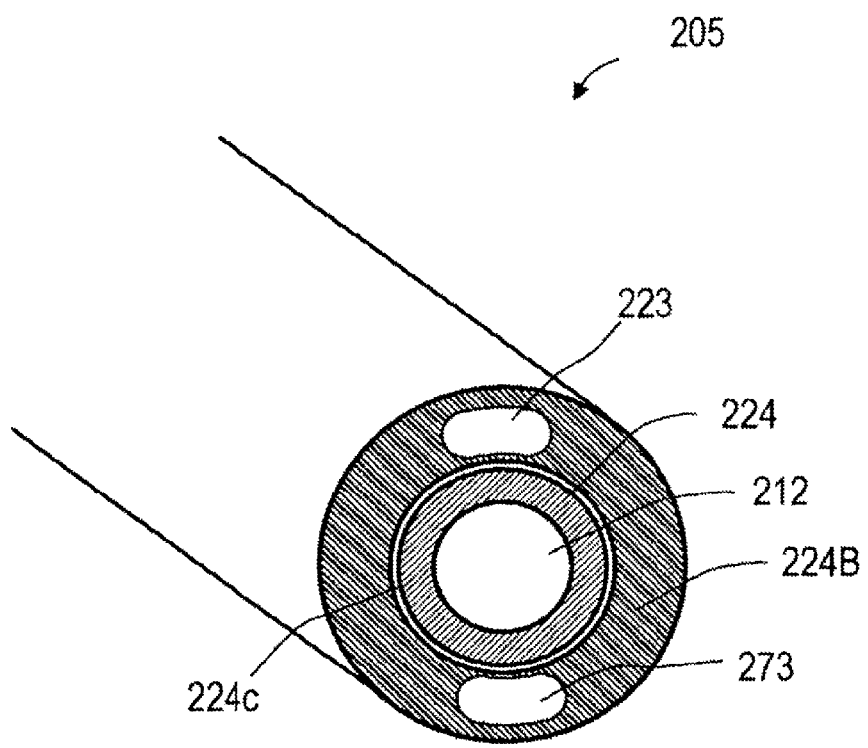
FIG. 10 is a sectional view of the catheter sleeve of FIG. 7.

In preferred embodiments of extension member 205 that comprise flexible endoluminal catheters, the member is fabricated of a single polymeric material or a combination of polymer layers 224a and 224b (FIG. 10). The exterior layer can have reinforcing in the form of braiding as is known in the art. In the embodiment of FIG. 10, the interior layer 224a is of a material having a low thermal conductivity, for example less than about 1.0 W/m-K, and preferably less than about 0.50 W/m-K. In one example, an unreinforced polyetheretherketone (PEEK) has a thermal conductivity of about 0.25 W/m-K and can be used for at least inner layer 224a of the extension member 205 FIG. 10). PEEK is high temperature resistant engineered thermoplastic with excellent chemical and fatigue resistance plus thermal stability. PEEK had a maximum continuous working temperature of 480° F. and retains its mechanical properties up to 570° F. in high-pressure environments. Other materials used in the extension member can comprise formulations or blends of polymers that include, but are not limited to PTFE, polyethylene terephthalate (PET), or PEBAX. PTFE (polytetrafluoroethylene) is a fluoropolymer which has high thermal stability (up to 260° C.), is chemically inert, has a very low dielectric constant, a very low surface friction and is inherently flame retardant. A range of homo and co-fluoropolymers are commercialized under such names as Teflon®, Tefzel®, Neoflon®, Polyflon® and Hyflon®. In another embodiment, the extension member or catheter 205 can carry another layer or structure 224e of any suitable thickness intermediate the inner and outer layers 224a and 224b that comprises a low thermal conductivity layer. Such a layer can comprise an air gap, insulative ceramic or glass microspheres or fibers, or at least one lumen that carries a cryofluid in communication with a cryogenic fluid source as in known in the art (see FIG. 10).

Figure 11:
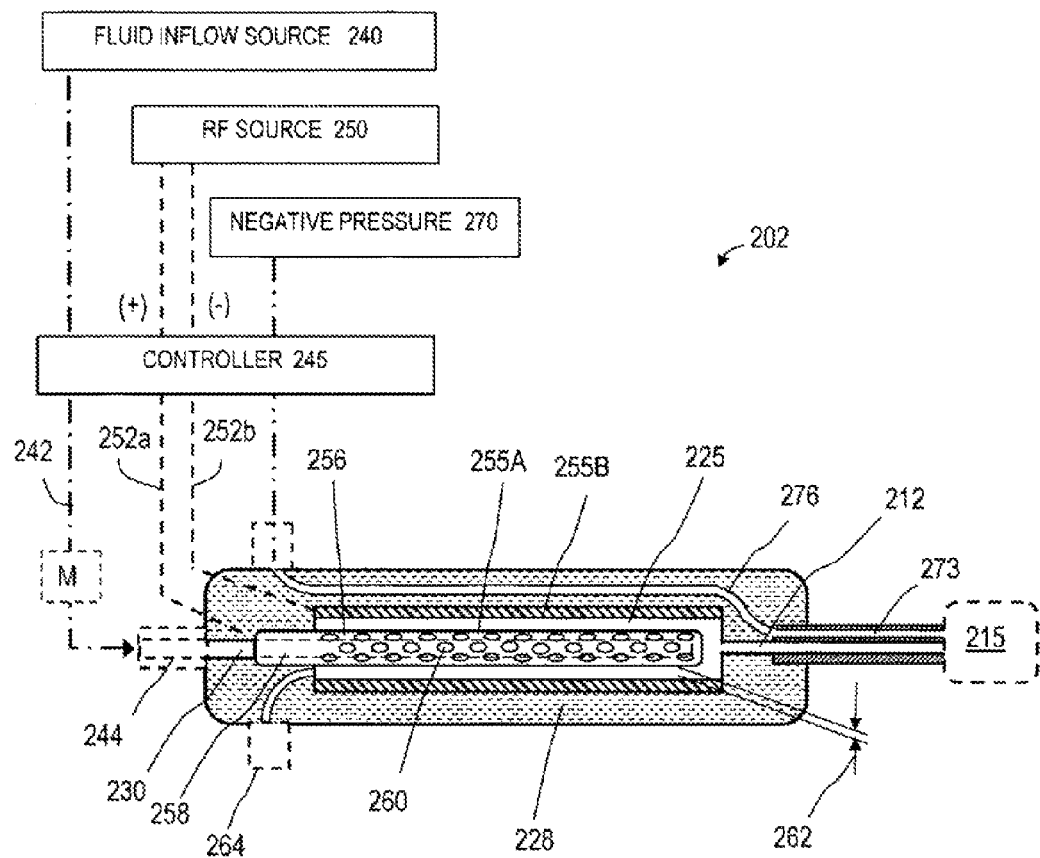
FIG. 11 is a cut-away view of the catheter handle of FIG. 7 depicting a thermal energy delivery mechanism for the liquid-to-vapor conversion of a pressurized inflow of a saline solution.

Now turning to FIG. 11, the cut-away view of the handle portion 202 of any of the embodiments of FIGS. 7-9B is shown. The handle 202 has an interior chamber 225 formed within the interior of an insulator material indicated at 228 such as a ceramic or a combination of materials to insulate the interior chamber 225 from the surface of the handle. An inflow channel 230 communicates with pressurized inflow source 240 of fluid or liquid media via flexible tube 242 coupled to fitting 244. A computer controller 245 is provided to control parameters of fluid inflows to interior chamber 225. The interior chamber 225 has a distal region in which media flows transition to outflow channel 212 that extends to a flexible or rigid extension member 205 and to an exemplary working end indicated at 215. In FIG. 11, it can be seen that Rf source 250 (also operatively connected to controller 245) has first polarity (+) lead 252a and opposing second polarity (−) lead 252b that are coupled respectively to first and second conductive surfaces or electrodes 255A and 255B exposed in interior chamber 225 that serve as a thermal energy delivery mechanism. The first conductive surface 255A is an inner or outer surface of elongated diffuser structure 256 having an interior bore 258 therein. Thus, the diffuser structure 256 defines a plurality of diffuser apertures or ports 260 in the wall of the structure for diffusing the flow of pressurized liquid media M into the interior chamber 225. The diffuser apertures or ports 260 have a suitable dimension and configuration for diffusing or atomizing a high pressure inflow of flow media M from source 240, which preferably is a saline solution. The second polarity (−) lead is coupled to conductive surface 255B which comprises a radially outward surface of interior chamber 225. In the embodiment shown in FIG. 11, it can be seen that the first and second conductive surfaces 255A and 255B are concentric, extend over a substantial length of the handle and have a large surface area with a fixed spaced apart radial dimension indicated at 262. In one embodiment, the radial dimension 262 between the electrode surfaces is selected to match the particular impedance and other operating characteristics of the Rf generator.

Referring to FIG. 11, in a method of operation, the system injects a volume of a conductive liquid such as hypertonic saline flow media M at a selected rate under pressure from source 240 which is diffused and atomized by ports 260 as the media enters interior chamber 225. Contemporaneous with injection and diffusion of the flow media, the system delivers sufficient current from source 250 and controller 245 to the conductive atomized saline via the opposing polarity surfaces 255A and 250B which instantly vaporizes the water in the flow media M to generate a non-ionized vapor M' that is injected from interior chamber 225 into lumen or channel 212 of the elongated extension member 205. The instantaneous Increase in volume of media in the liquid-to-vapor phase transition greatly increases interior pressures in interior chamber 225 to thereby accelerate the flow into and through the extension member 205 to a least one open termination in the distal end of the member 205. As shown in FIG. 11, the system and handle can include an optional pressure relief valve schematically indicated at 264 so that any overpressures in the interior chamber are released. The release of any overpressure can be vented through an additional lumen in the supply tube 242 or to another chamber in the handle 202.

Referring to FIGS. 7, 8A and 9A, the system optionally includes a negative pressure source 270 that communicates with another lumen 273 in catheter sleeve 205 that has an open distal termination in the working end 215 of the extension member 205. The handle 202 further has a suitable channel indicated at 276 that extends between the negative pressure source 270 and aspiration lumen 273 in extension member 205.

Figure 12:
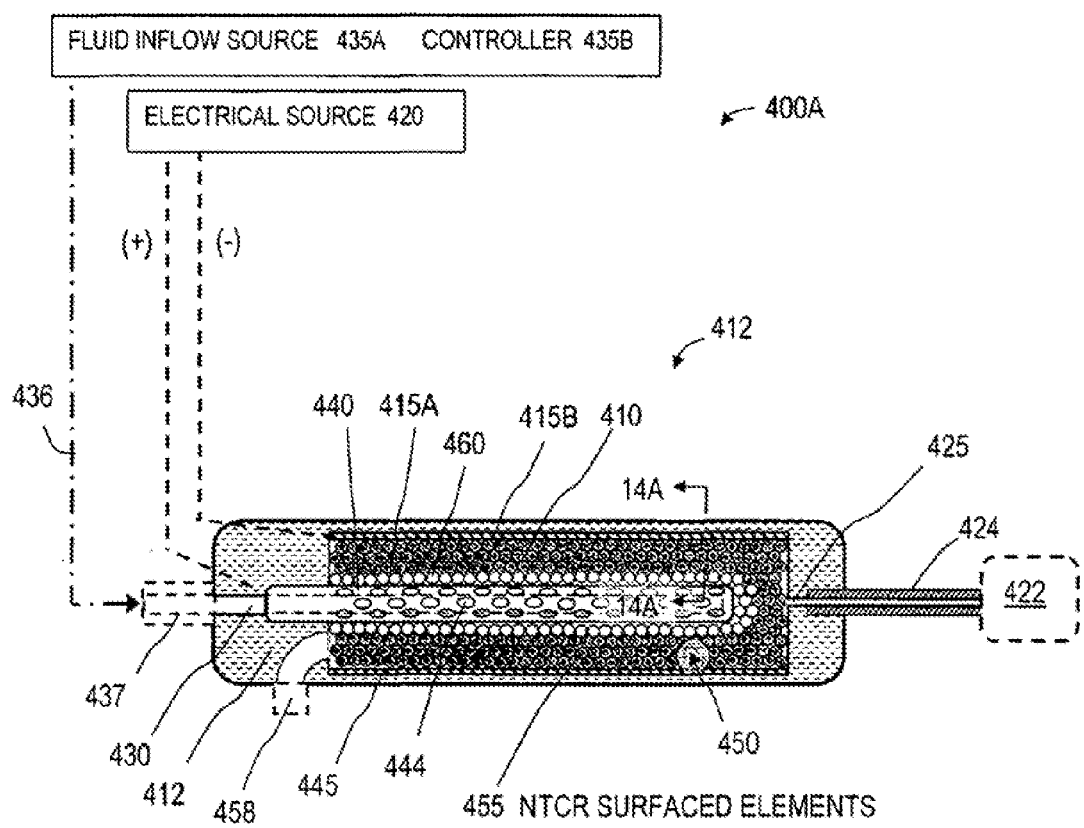
FIG. 12 is a cut-away view of an alternative system embodiment that utilizes a negative temperature coefficient of resistance (NTCR) material for modulated energy delivery to inflowing media between conductive heating of the media and $I^2R$ heating of the media to cause vaporization thereof.

Now turning to FIG. 12, another system embodiment 400A is shown wherein an interior chamber 410 again in disposed in a handle portion 412 of the instrument that includes opposing polarity conductive components 415A and 415B that function as the thermal energy delivery mechanism. It should be appreciated that the components of the system can also be reduced in scale to be positioned in an elongated extension member 205 as in FIGS. 7, 8A and 8B. In the system embodiment of FIG. 12 and related versions that follow in FIGS. 13-21, the systems include the use of temperature coefficient materials for optimizing energy delivery to a conductive flow media (such as saline solution) from a radiofrequency (Rf) source 420. The working end 422 of the system is shown schematically and includes an elongate member 424 with at least one lumen 425 for carrying vapor media to exit a working end surface for interfacing with targeted tissues or body structure, including but not limited to (i) a needle for penetrating soil tissue, (ii) a blunt-tipped probe for painting across a tissue surface or interior body surface such as joint tissue; (iii) a punch or threaded tip for penetrating into hard tissue such as bone to treat a tumor, avascular necrosis or the like; (iv) an elongate flexible probe or catheter device for endoluminal energy delivery; (v) a balloon, a flexible film or expandable surface for engaging body structure, (vi) any jaw structure or approximating components for capturing tissue; or (vii) any blade edge, cutting loop or rotatable element for cutting tissue.

Figure 13:
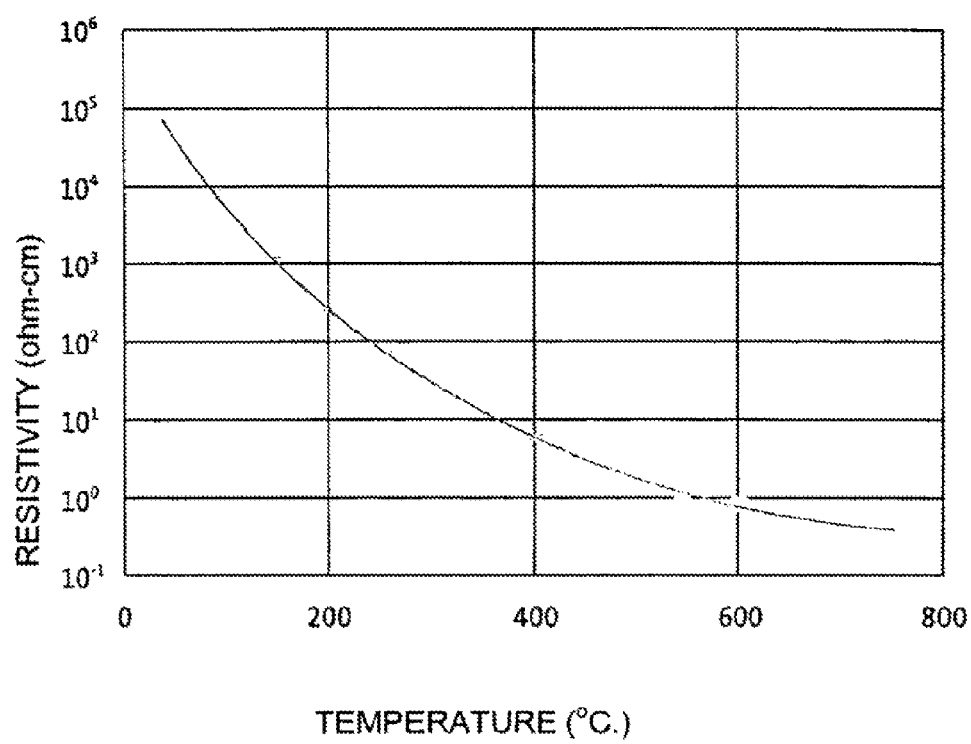
FIG. 13 is an temperature resistance curve of the NTCR material of FIG. 12.

In FIG. 12, the handle 412 is fabricated with an insulator material indicated at 428 that surrounds interior chamber 410. An inflow channel 430 communicates with the inflow source 435A of fluid media M and pressure control system 435B via flexible tube 436 coupled to fitting 438. The interior chamber 410 has a distal region in which media flows transition to outflow channel 425 that extends to the working end 422. In FIG. 12, it can be seen that the first polarity (+) lead is coupled to a closed end elongated diffuser structure 440 of which at least a portion comprises the first conductor 415A. The diffuser structure 440 has diffuser ports 444 about and along its length that have a suitable dimension and configuration for diffusing or atomizing a high pressure inflow of saline media M into small cross-section flows. The second polarity (−) lead is coupled to conductive sleeve 445, the surface of which comprises the second polarity conductor 415B about the radially outward surface of interior chamber 410. Of particular interest, the interior chamber 410 is occupied in part by a flow permeable structure 450 that has negative temperature coefficient of resistance (NTCR) properties—and in this case comprises packed together porous silicon carbide microspheres indicated at 455. Such NTCR flow permeable structures 450 in the form of assembled porous elements, porous or non-porous rods, tubes, sleeves and the like are available from Saint-Gobain Ceramics, 23 Acheson Drive, Niagara Falls, N.Y. 14303 USA. The NTCR properties of an exemplary silicon carbide are shown in FIG. 13, wherein the resistivity in ohms-cm rapidly decreases by orders of magnitude in a selected temperature range between about 100° C. and 600° C. Further, the NTCR flow permeable structure 450 is spaced apart from structure 440 and first polarity conductor surface 415A by a space or by non-conductive ceramic or glass microspheres 460 as depicted in FIG. 12. Suitable non-conductive spheres are available from Saint-Gobain Ceramics, 23 Acheson Drive, Niagara Falls, N.Y. 14303 USA or under the trade name SPHERIGLASS® from Potters Industries, Inc. P.O. Box 840, Valley Forge, Pa. 19482-0840. The NTCR structures can be fabricated from various materials besides silicon carbide, such as tungsten carbide, boron carbide, boron nitride, zirconia or combinations or assemblies thereof, or doped germanium or silicon glass composites. The flow permeable structure 450 alternatively cart comprise structures, elements or assemblies of a non-conductive glass or ceramic that is coated with any suitable NTCR material.

Still referring to FIG. 12, in a method of operation, the system injects liquid saline media under pressure from source 435A which is diffused by the atomization ports 444 in the diffuser structure. The high pressure flow of diffused saline is then within the reduced cross-section open pathways of the flow permeable structure 450. Contemporaneous with injection and diffusion of the saline, the system delivers sufficient Rf current from source 420 to the conductive atomized saline via the opposing polarity surface conductors 415A and 415B to instantly elevate $H_2O$ in the media to cause a liquid-to-vapor phase change therein (via $I^2R$ or Joule heating). The instantaneous increase in volume of the vapor phase media greatly increases interior pressures to thereby accelerate the media flow in the distal direction in and about the flow permeable structure 450 through outflow channel 425. The system includes an optional pressure relief valve schematically indicated at 458 in FIG. 12. The system also can include a check valve (not shown) in inflow channel 430 for preventing backflows when the system is turned on and off.

Figure 14A:
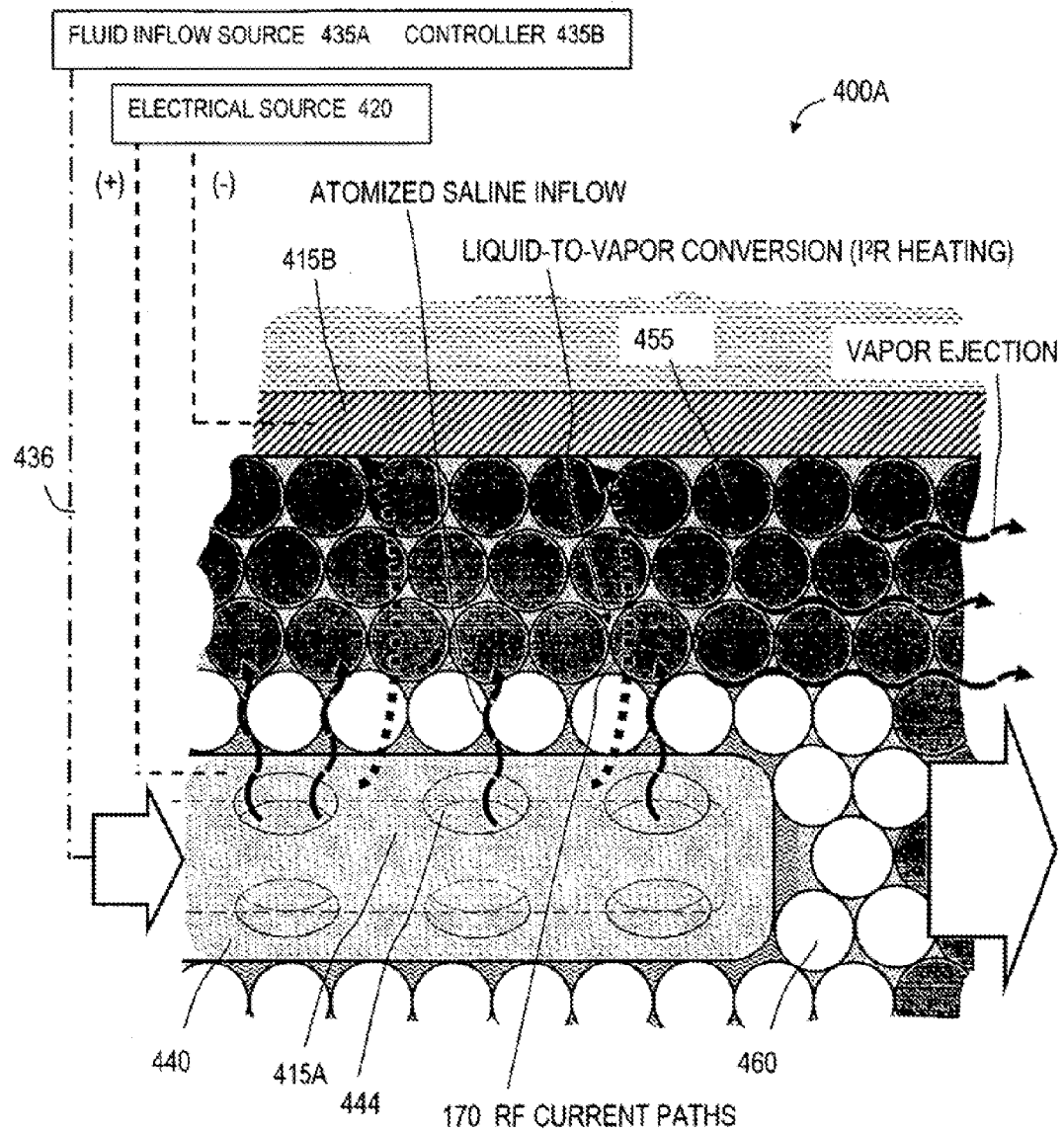
FIG. 14A is an enlarged sectional view of the system of FIG. 12 showing operational characteristics thereof.
Figure 14B:
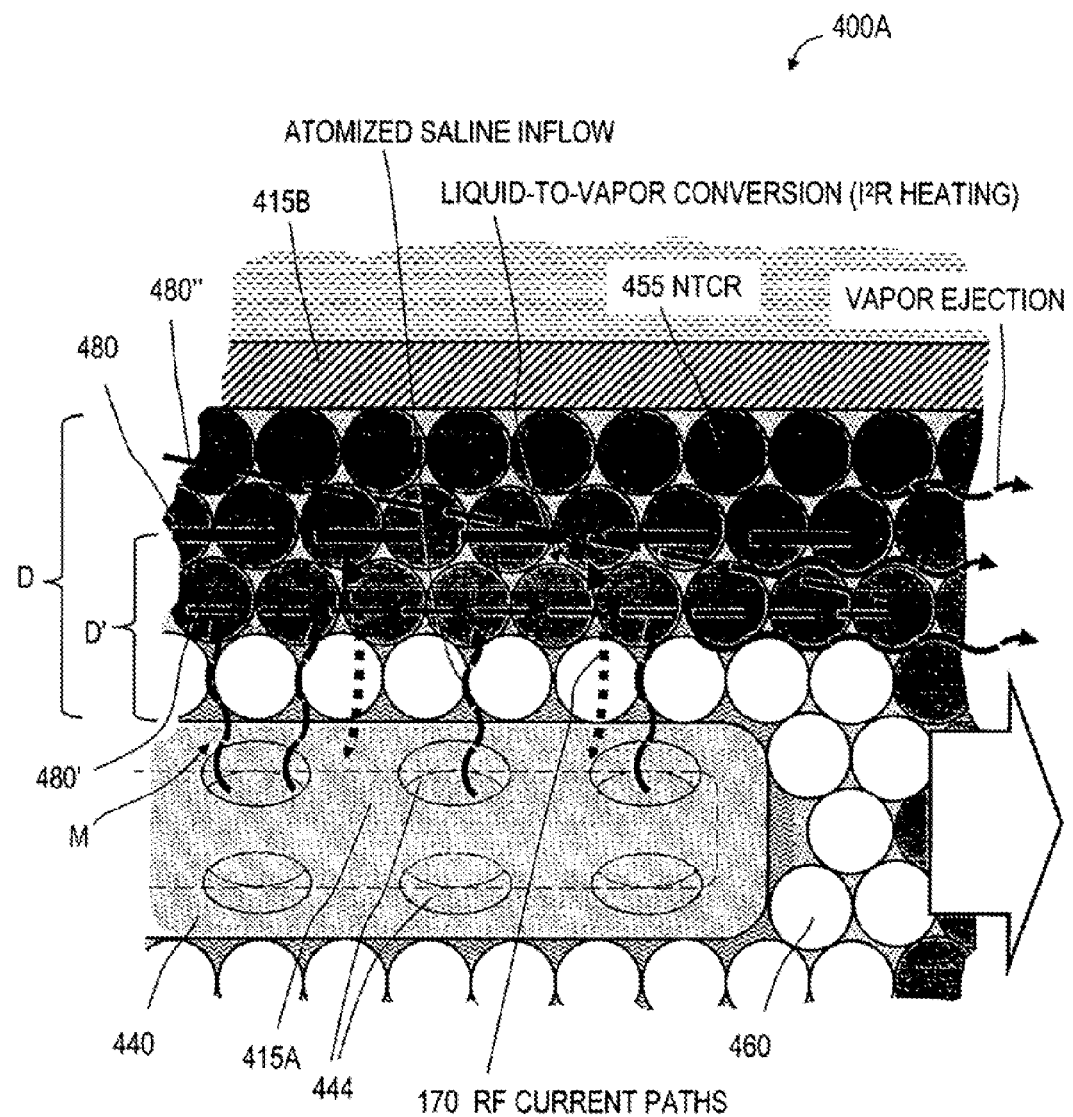
FIG. 14B is an enlarged sectional view of a system similar to FIG. 12 showing operational characteristics thereof.
Figure 15:
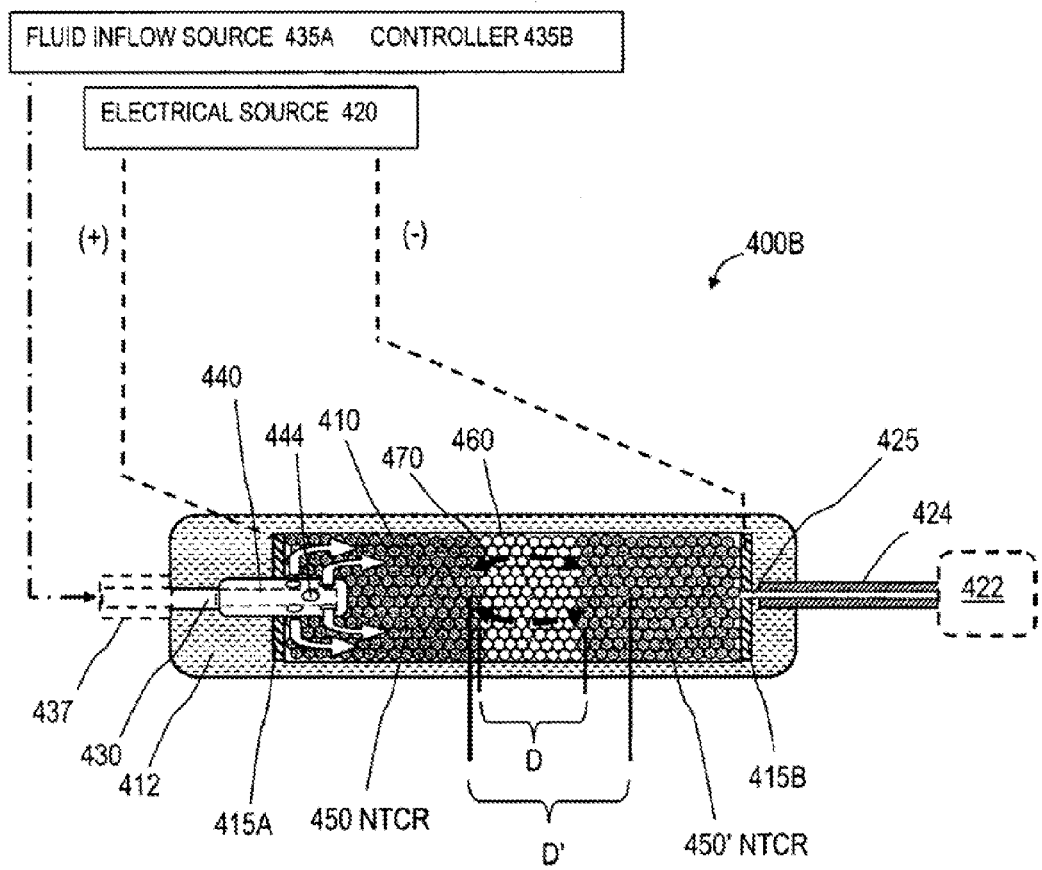
FIG. 15 is a cut-away view of an alternative embodiment that utilizes a NTCR material for delivering the heat of vaporization to inflowing liquid media.
Figure 16:
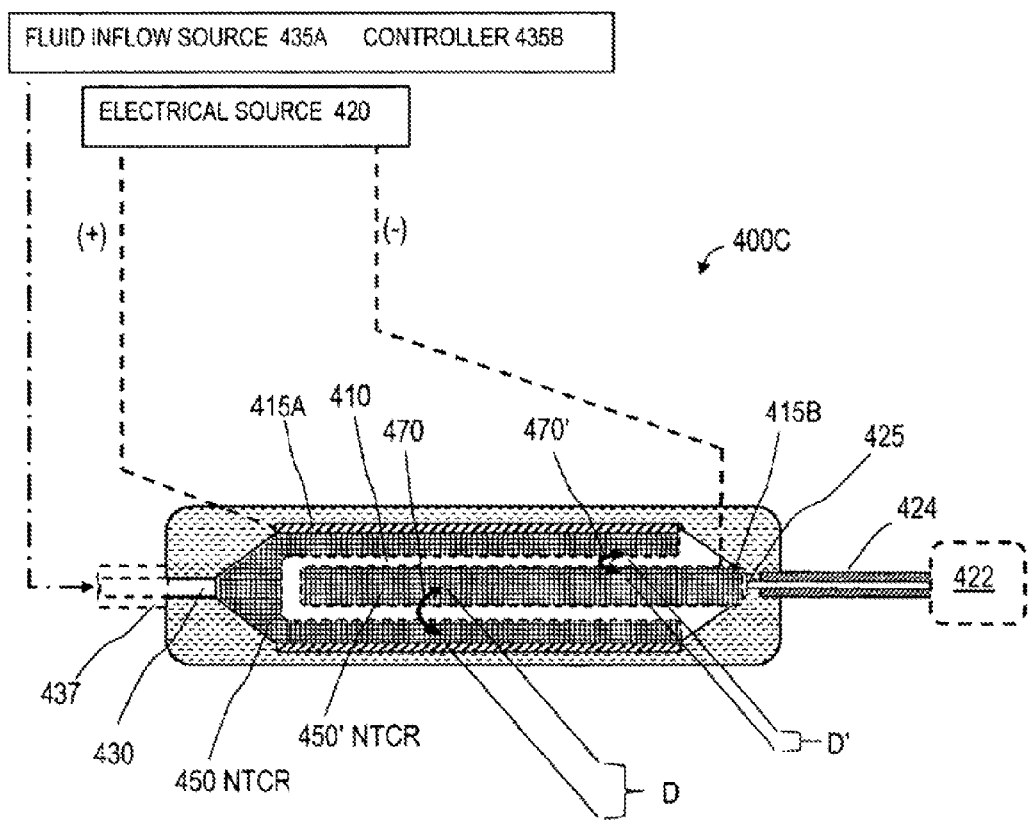
FIG. 16 is a cut-away view of an alternative embodiment for delivering the heat of vaporization to inflowing liquid media.

Of particular interest, during operation of the system, the Rf current flow in the interior chamber 410 and flow permeable structure 450 of FIG. 12 will seek a path of least resistance between the opposing polarity surface conductors 415A and 415B, which is shown in an enlarged schematic views in FIGS. 14A and 14B as dashed lines of current paths 170. An initial intense application of Rf energy will initially cause ohmic heating ($I^2R$ or Joule heating) and vaporization of the atomized saline within the flow permeable structure 450—with the arc of current effectively flowing from the surface coil doctors 415A and 415B as indicated in FIG. 14A.

Referring now to FIG. 14B, at the same time that the saline is vaporized (as in FIG. 14A), the vapor media will elevate the temperature of the NTCR flow permeable structure 450 thus reducing its resistivity to cause some current flow therein. The regions of the NTCR structure from which the current couples with the conductive fluid will have the highest instantaneous temperature and hence lowest resistance. The operation of the system thus cause a reduced resistivity region so that current paths 170 are allowed to adjust in length dynamically. It is believed that the result will be that current path lengths will self-adjust optimally to the particular output, waveform and operating characteristics of the Rf generator used to deliver energy to the system. As depicted in FIG. 14B, a particular Rf generator will delivery power optimally to the atomized media across a certain dimension D, for example between points 415A and 415B—assuming certain other operating parameters such as atomized saline inflow rates and volumes, interior pressures determined by permitted outflow rates, and the specified resistivity of the saline media. Another particular Rf generator would deliver power optimally across a different dimension between opposing polarity surface, for example D' and surface region 480'. Preferably, the interior chamber dimensions can be designed to match the computed optimal operating, characteristics and impedance of a particular generator, such as dimension D in FIG. 14B. The improved system of the invention uses NTCR surfaces or an NTCR flow permeable structure 450 as in FIGS. 12, 14A and 14B that has selected resistivity-temperature characteristics, wherein the NTCR surfaces will effectively self-adjust the average dimension between spaced apart surface portions or regions (e.g., 415A and 480-480') that apply energy to the inflowing saline media during operation of the system. Thus, the NTCR surfaces can self-adjust the average dimension between spaced apart surface portions, for 415A and 480' in FIG. 14B when the vapor phase media's resistance is lowered, the flow velocity is increased or when other such operation parameters are changed by external controls or by Rf energy delivery and Joule heating itself. Further, the NTCR surfaces will allow for different "radial" dimensions between the effective opposing polarity conductor surfaces over an axial length of the interior chamber 410 during operation as schematically indicated by line 480" in FIG. 14B. Still further, the NTCR surfaces will resistively heat and thereby deliver heat to the atomized saline by means of conduction in addition to Joule heating to enhance energy delivery for the liquid-to-vapor conversion in chamber 410.

FIG. 15 illustrates an alternative embodiment of system 400B wherein the opposing polarity leads are coupled to axially spaced apart conductive surfaces 415A and 415B, rather than the radially spaced apart surfaces in the embodiment of FIGS. 12 and 14A-14B. In FIG. 15, it can be seen that the saline media M is introduced into the interior chamber 410 through closed end sleeve 440 and atomized by diffuser ports 444. In this embodiment, the interior chamber 410 has first, and second NTCR flow permeable structures 450 and 450'—which again can be packed together porous silicon carbide microspheres indicated at 455. The NTCR structures 450 and 450' are spaced apart by a flow permeable electrically insulative material such as ceramic microspheres 460. In this embodiment, the NTCR structure can be designed for rapid internal resistive heating. In use, inflowing atomized liquid that reaches the fluid permeable region around the insulative microspheres 460 will then be instantly vaporized by a combination of $I^2R$ heating of the resistive saline components (current paths 470) and the conduction of heat from the very high surface area of the internally heated NTCR structure to the media. The system of FIG. 15 thus has two NTCR flow permeable structures 450 and 450' that can self-adjust the average dimension between the spaced apart surface portions, for example D and D', that apply Rf energy to the inflowing media M during operation of the system. This system again can self-adjust the changing resistivity of the vapor phase media as it propagates distally at high velocity, and other operation parameters such as the pressure and volumes of media inflows per unit time. Thus, the liquid-to-vapor conversion in chamber 410 will occur dynamically over a range of interior regions of the device during operation. It should be appreciated that the NTCR structures also can be designed to have a gradient in NTCR properties (i.e., temperature-resistance curves as in FIG. 13) between the opposing polarity surfaces 415A and 415B to induce current arcing through the inflow media M about selected geometries with operational arcing geometries changing during operation.

FIG. 16 illustrates another system embodiment 400C wherein the opposing polarity leads are coupled to radially spaced apart conductive surfaces 415A and 415B that couple to the fluid permeable diffuser structures such as a syntactic material or open-cell material. The terms "syntactic", "open-cell" and "flow-permeable" as used herein refer to any structure that has substantial porosity for allowing fluid flow therethrough. Such materials have the advantage of providing very high surface areas (i) for conducting heat from an $I^2R$ heated material to pressurized media flows therein, or (ii) for conducting Rf current into a conductive media to cause $I^2R$ heating and vaporization of the media. The open-cell material can be a foam, sintered material, a plated entangled filament material, a microchannel structure or any ordered or disordered structure with flow passageways therein. For example, syntactic metals and ceramics are available from ERG Materials and Aerospace Corp., 900 Stanford Avenue, Oakland, Calif. 94608 and Poco Graphite (http://www.poco.com).

In the embodiment of FIG. 16, at least one and preferably both of the syntactic structures have NTCR surfaces 450 and 450' or are fabricated of an NTCR material. The syntactic structure is further selected to provide an internal pore dimension that causes diffusion and small cross-section flows of the saline media M as it is introduced into interior chamber 410 through channel 430 to thus function as the diffuser ports 444 in previous embodiments (see FIG. 12).

Of particular interest, the NTCR materials of the embodiment of FIG. 16 will cause current flows into and across the following conductive media to cause $I^2R$ heating and vaporization thereof—and during operation the mean dimension of the current path can transition from path 470 (dimension D) to path 470' (dimension D') as the impedance and velocity of the media changes. It is believed that the NTCR structures will cause current to jump preferentially from a particular location on the structure into the media based on the operating parameters of the Rf generator to cause a current path of a selected length, which in turn will cause very high heating of the particular location of the NTCR material which will further cause the resistance of the material to lower at the particular location. During operation, as the velocity and impedance of the liquid-to-vapor converting media changes, the particular location(s) on the NTCR structure that current jumps to or from can transition both radially and axially to match the operating parameters of the Rf generator.

FIG. 17 illustrates another system embodiment 400D wherein the opposing polarity leads and conductive surfaces 415A and 415B are spaced apart axially and are coupled to syntactic structures having NTCR surfaces 450 and 450' or wherein the structures are fabricated of an NTCR material. The system of FIG. 17 will operate based on the principles described above with reference to FIG. 17. During operation, as the changing velocity and impedance of the liquid-to-vapor conversion is ongoing, the NTCR structures can self-adjust the axial dimension of the jump of Rf current to match the operating parameters of the Rf generator. In another similar embodiment, the syntactic structures can be fabricated of a positive temperature coefficient of resistance (PTCR) ceramic or other material, which will conduct current to a conductive flow media with the conductive surface portions of the material changing during operation. Thus, the NTCR material delivers thermal energy to inflowing by conduction and then by Rf ohmic heating of the liquid wherein a PTCR material delivers energy to the inflowing liquid initially by ohmic heating of the liquid and subsequently by conduction from the PTCR material to the liquid.

Figure 17:
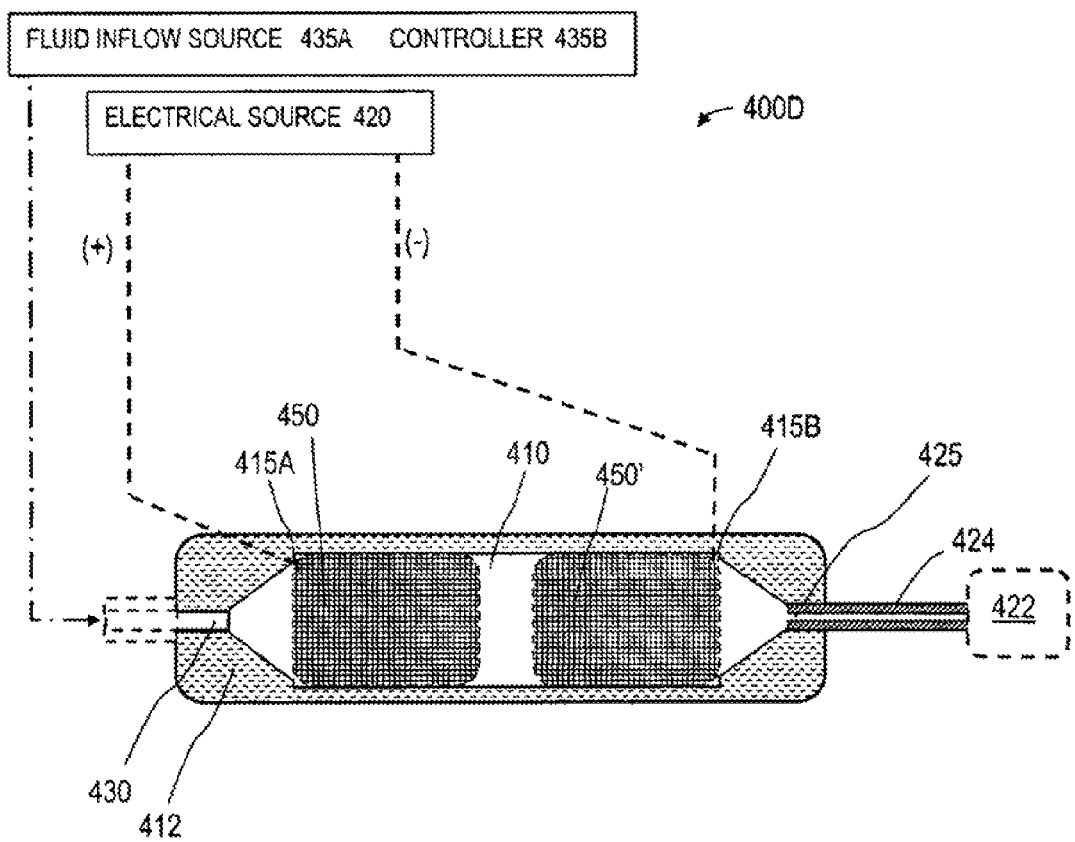
FIG. 17 is a cut-away view of an alternative embodiment for delivering the heat of vaporization to inflowing liquid media.
Figure 18:
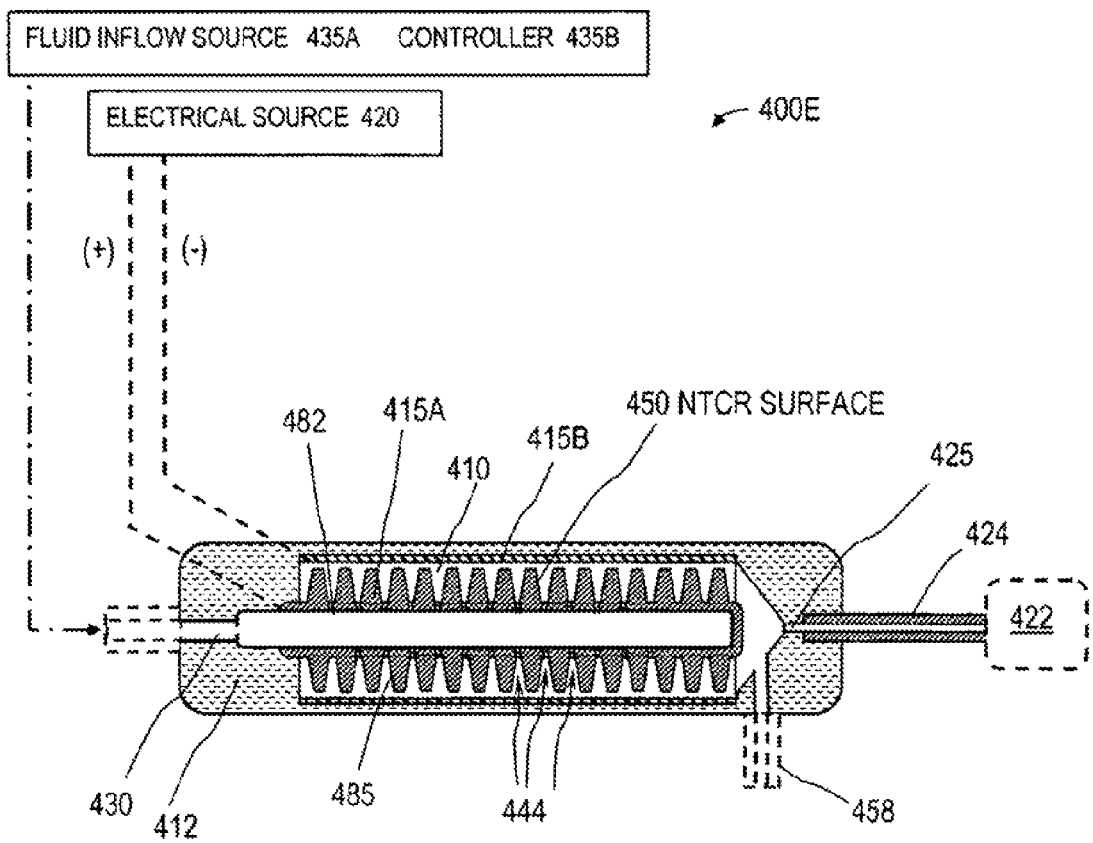
FIG. 18 is a cut-away view of an alternative embodiment for delivering the heat of vaporization to inflowing liquid media.

FIG. 18 illustrates another system embodiment 400F wherein the opposing polarity leads and conductive surfaces 415A and 415B are spaced apart radially. In this embodiment, rather than providing a syntactic structure with larger surface areas, a central structure 482 is provided that has fins, projections or other such elements indicated at 485 for providing substantially high surface areas and for providing surfaces that provide for varied dimension current paths to thus operate on the principles described above with reference to FIG. 17. The tins 485 have NTCR surfaces 450 as described above and again the structure provides diffusion ports 444 for atomizing saline inflows. The tins or projecting elements 485 can have any suitable configuration and dimension such as radial elements, helical elements, axial elements or a combination thereof and can extend from either or both the surface of the chamber 410 or from a central member 482 in the chamber.

Figure 19:
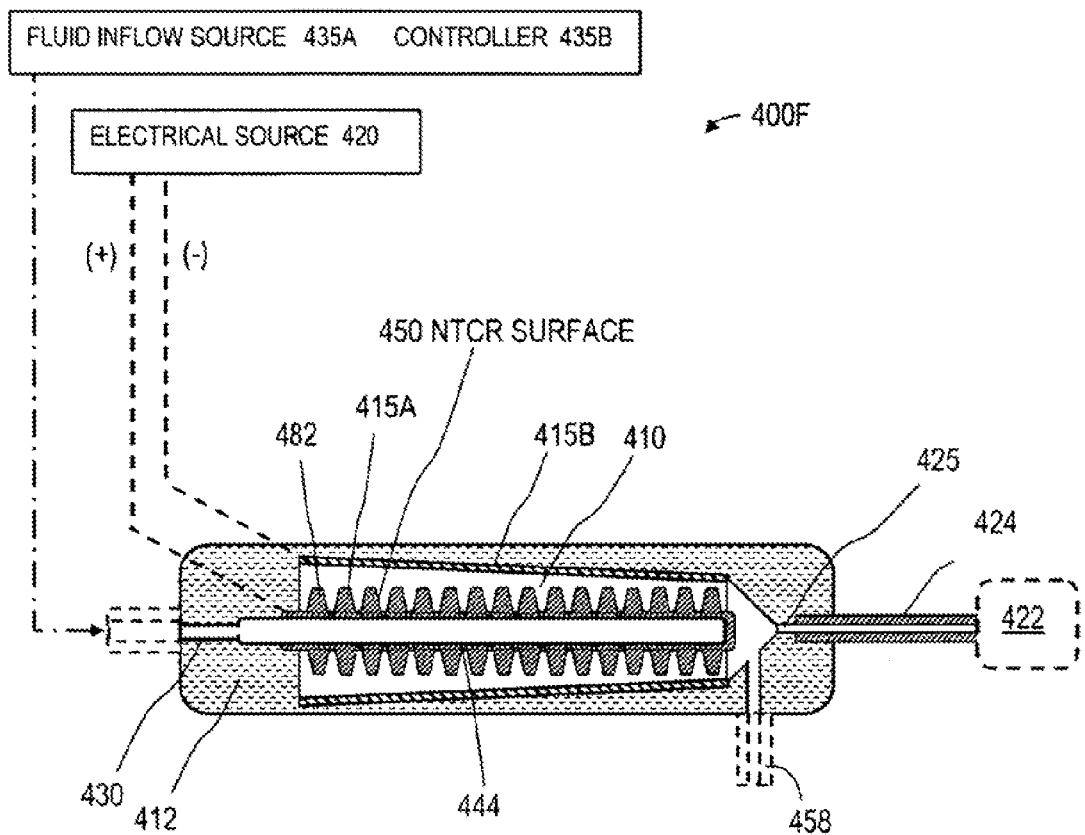
FIG. 19 is a cut-away view of an alternative embodiment for delivering the heat of vaporization to inflowing liquid media.

FIG. 19 illustrates another system embodiment 400F which operates as the embodiments of FIGS. 17 and 18 except the conductive surface 415B is tapered to provide a wider range of radial dimensions extending axially over the length of the interior chamber.

Figure 20:
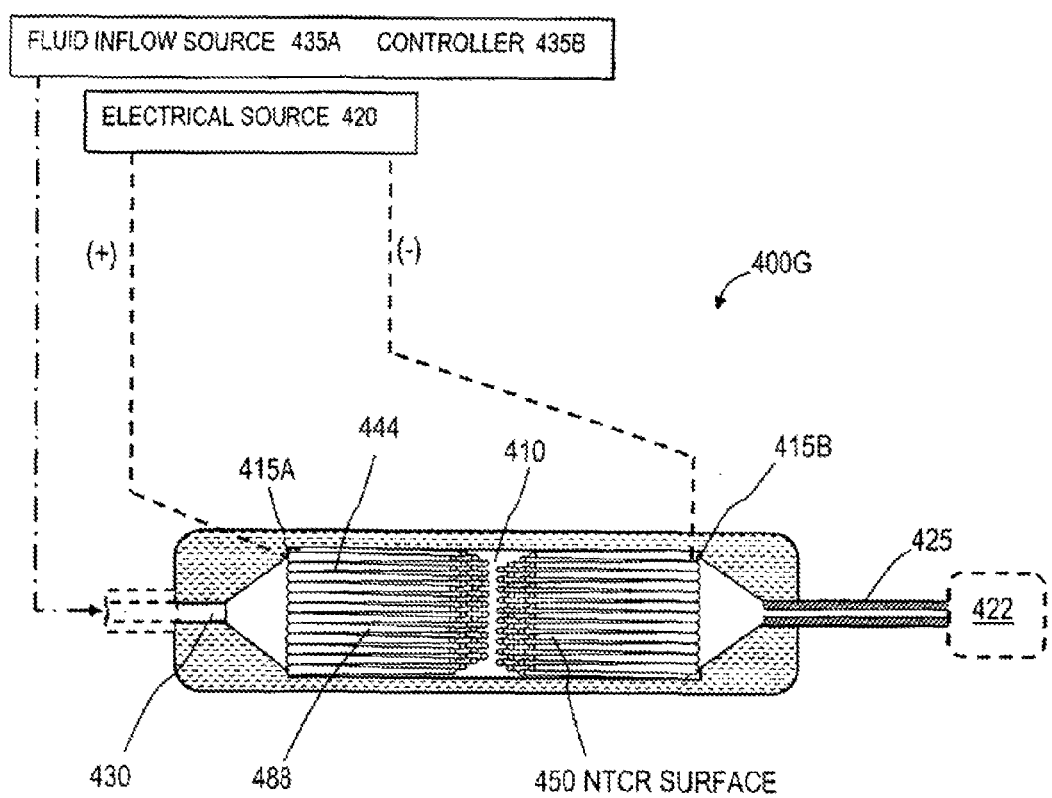
FIG. 20 is a cut-away view of an alternative embodiment for delivering the heat of vaporization to inflowing liquid media.

FIG. 20 illustrates another system embodiment 400G which operates as the embodiments of FIGS. 17-19 except the conductive surfaces are carried by a plurality of assembled or packed together linear filaments 488 which can be tapered or flexible as in wire elements. Gaps between the elements 488 provide diffusion ports 444 thus providing a diffuser structure as described previously.

Figure 21:
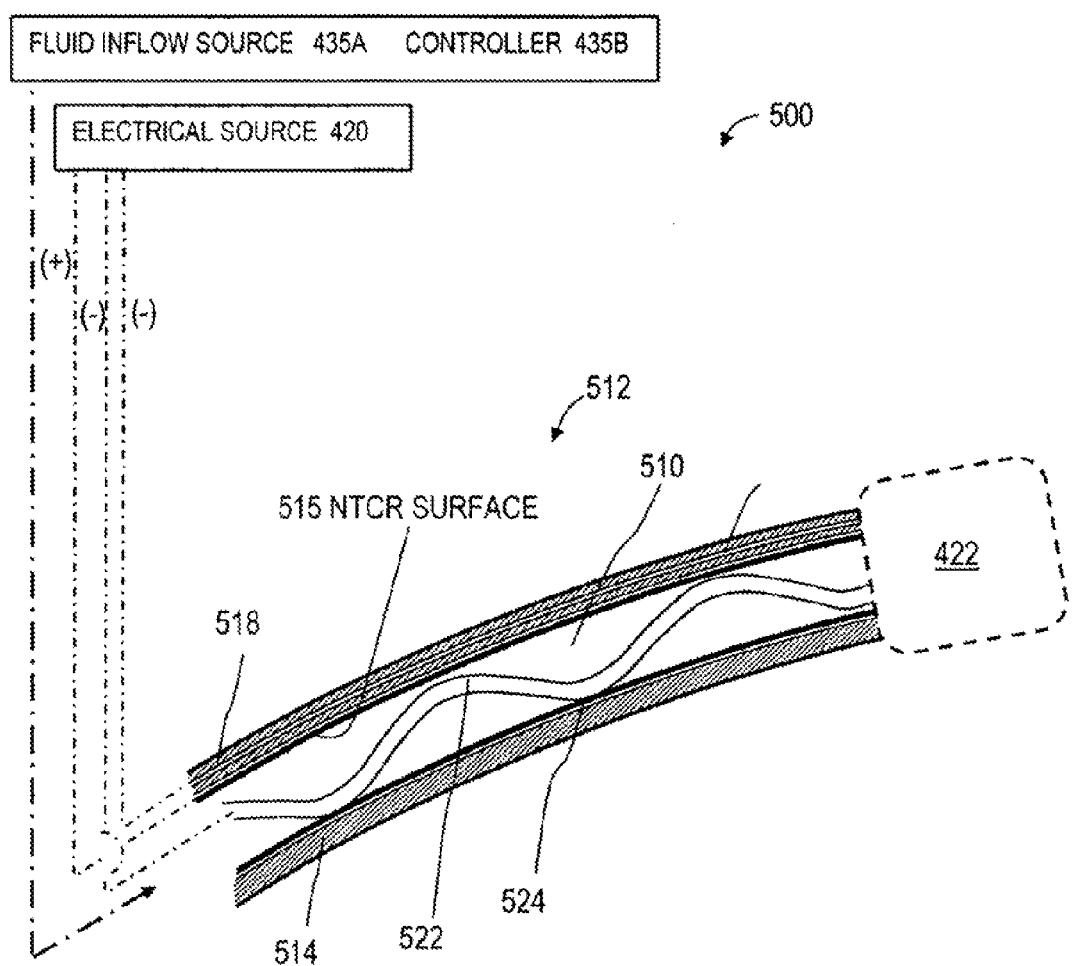
FIG. 21 is a cut-away view of a working end of as catheter sleeve that is configured for delivering the heat of vaporization to inflowing liquid media.

FIG. 21 illustrates another system embodiment 500 which includes components and features as in the embodiments of FIGS. 12-20 except that the configuration is adapted for the working end of a small diameter rigid probe or a flexible catheter, in FIG. 21, the interior chamber 510 comprises an elongate lumen of a member 512 having an insulated wall 514. A flow diffuser is located in a proximal portion of lumen 510 (not shown). In one embodiment, the interior of the lumen 510 comprises an NTCR surface indicated at 515. The NTCR surface 515 is coupled to insulated lead 518 and the Rf source 420 to thus comprise a series circuit. NTCR surface 515 is capable of internal $I^2R$ heating to thereby cause heating and vaporization of media flows in the lumen. A conductive filament 520 is carried in lumen 510 with the filament having kinks or bends 522 so that the filament does not continuously contact the NTCR surface. The filament 520 is electrically conductive and is coupled to the Rf source to provide a parallel circuit when Rf current jumps from surface 515 to the filament 520 through the conductive media which thereby vaporizes the media. In operation, the NTCR surface 515 will tend to cause current flow into the filament 520 at contact points 524 but inflowing media M will cool that location inducing the current to flow into the media and thereby vaporize the media. A plurality of such filaments 520 can be carried in a microchannel structure as described above—with a single filament in each microchannels. In another embodiment, the filament 920 also can have an NTCR surface.

In another embodiment similar to FIG. 21, the interior surface of lumen 510 and/or the filament can comprise a positive temperature coefficient of resistance (PTCR) material. In operation, the PTCR materials would not internally heat but would be adapted to only cause $I^2R$ heating of the fluid media M itself within the lumen for causing the liquid-to-vapor conversion.

Figure 22:
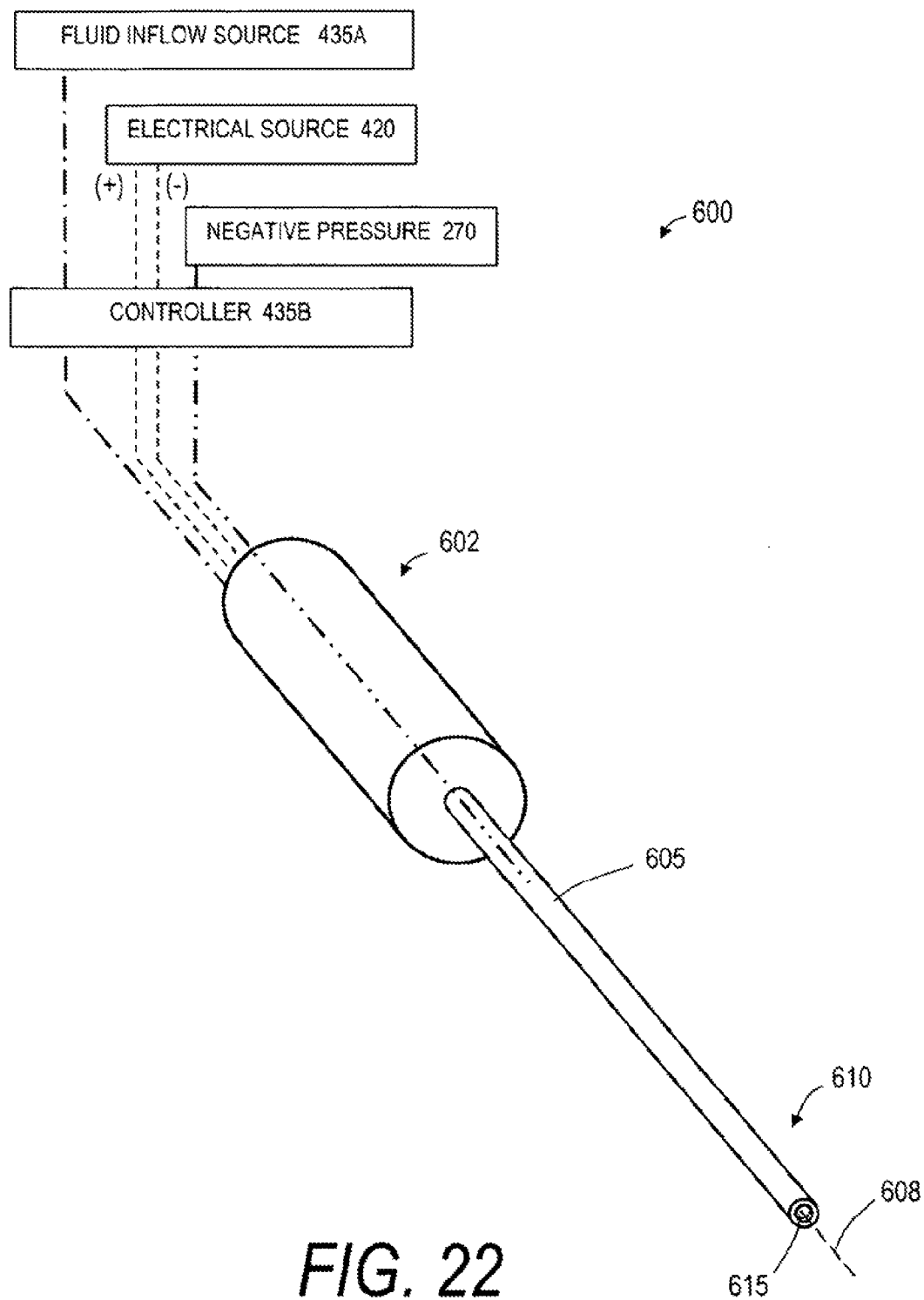
FIG. 22 is as perspective view of another probe embodiment configured for tissue extraction.
Figure 23:
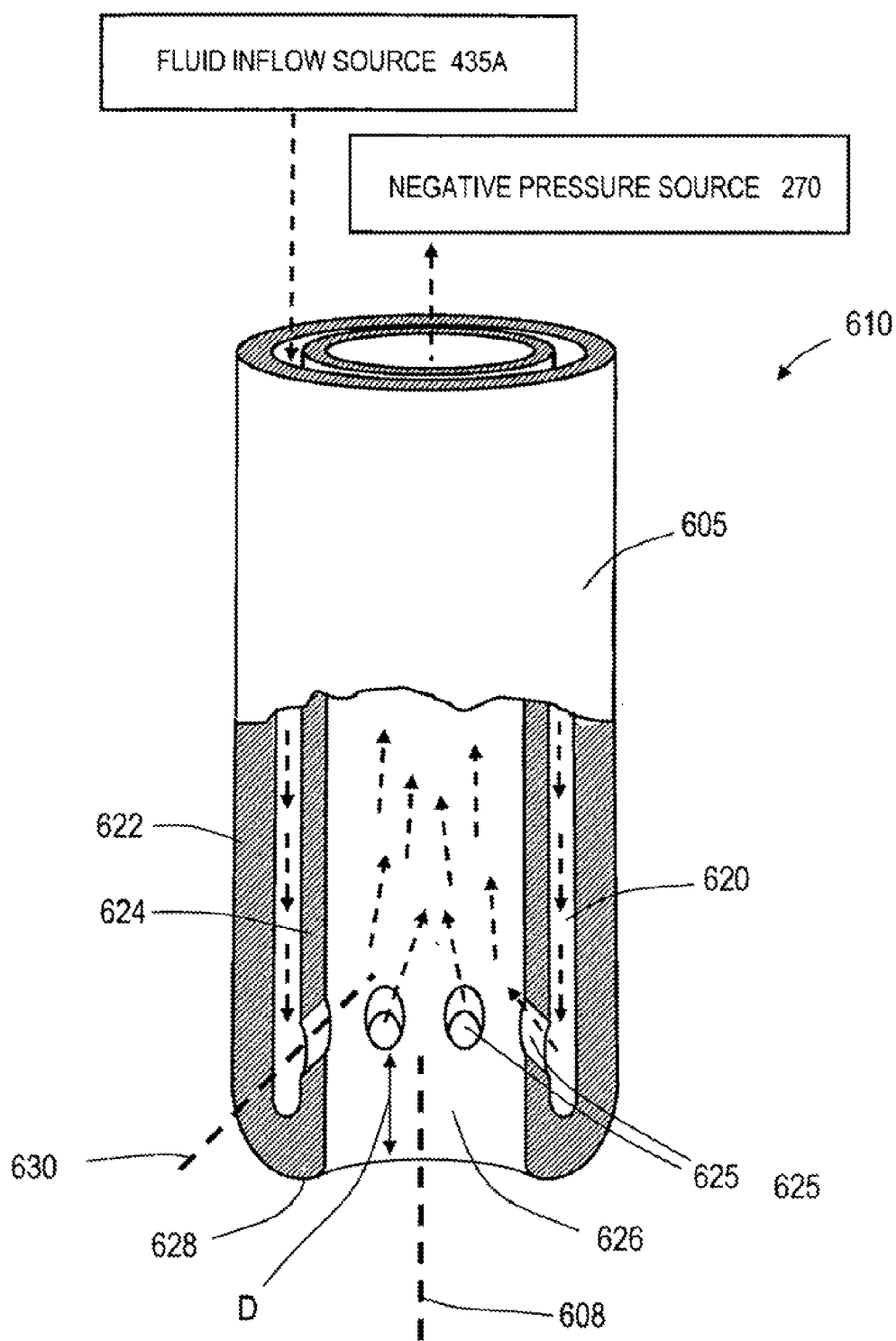
FIG. 23 is an enlarged cut-away view of the working end of the probe of FIG. 22.

FIG. 22-24 illustrate another probe embodiment 600 that is adapted for tissue ablation, tissue disintegration and tissue extraction. The probe has a handle portion and vapor source that is similar to any of the handle embodiments of FIGS. 7, 11, 12, and 14-20 for providing a flow of a vapor media. Probe 600 of FIG. 22 has electrical source 420, fluid inflow source 435A and controller 435B as described with reference to FIGS. 12 and 14-20. Probe 600 also has a negative pressure source 270 as described generally with reference to FIGS. 7 and 11 above.

Figure 24A:
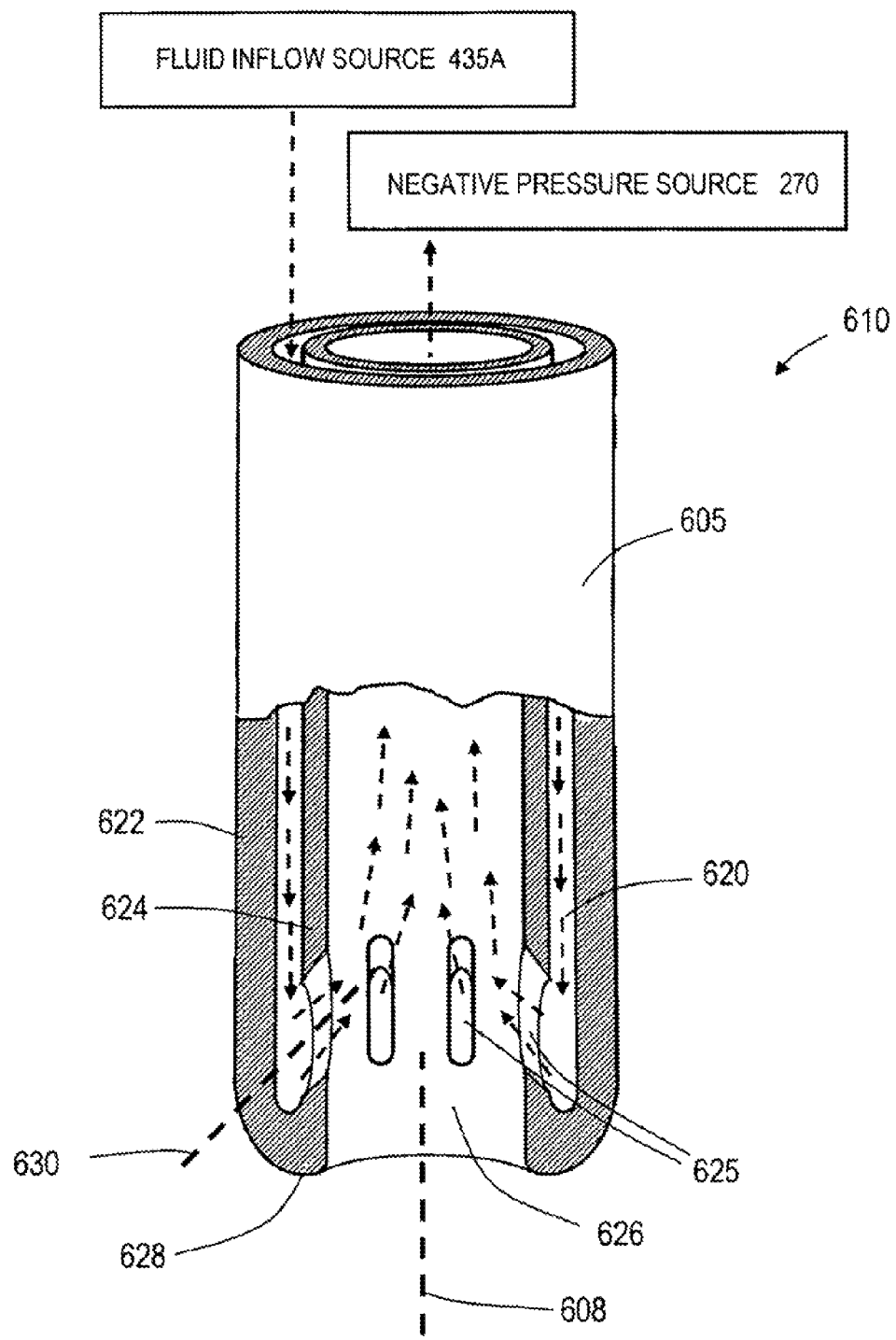
FIG. 24A is an enlarged cut-away view of an alternative working end similar to the probe working end of FIG. 22.
Figure 24B:
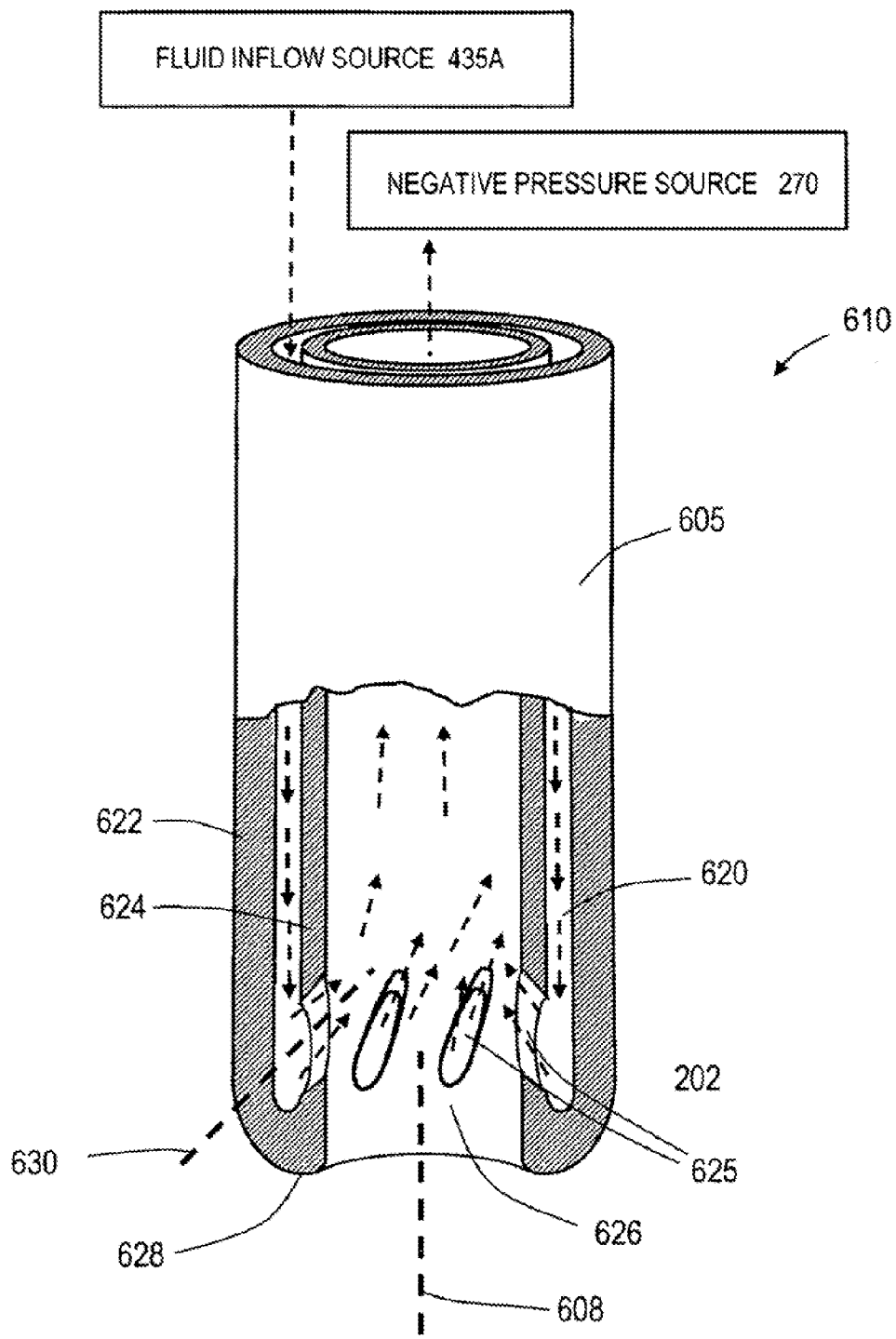
FIG. 24B is an enlarged cut-away view of another working end similar similar to that of FIG. 22.
Figure 25:
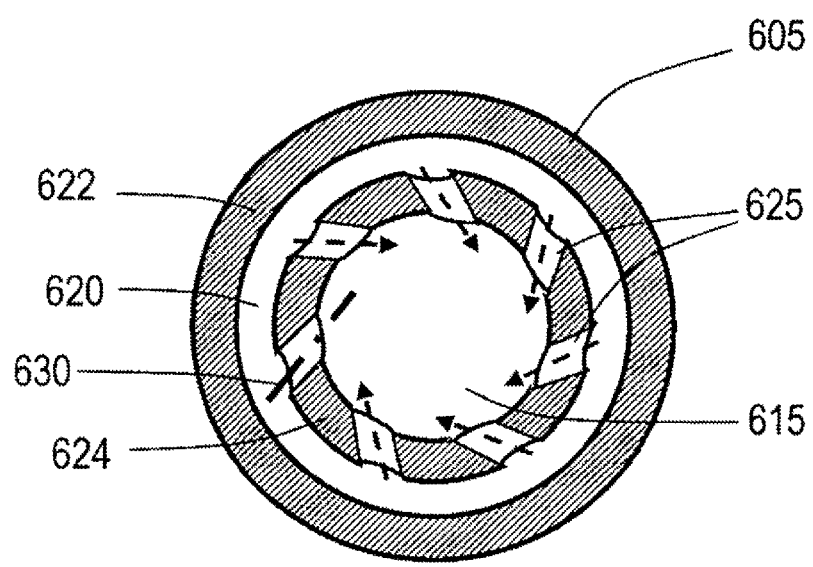
FIG. 25 is a cross-sectional view of the working end of FIG. 22.

The probe 600 of FIG. 22 has handle portion 602 that transitions to extension member 605 having axis 608 that extends to working end 610. The probe 600 has a central aspiration lumen 615 extending through the probe body to an open distal termination. The probe has a vapor flow channel 620 for providing a flow of vapor to working end 610 that is configured as a concentric channel between first and second walls, 622 and 624 respectively, surrounding the aspiration channel 615 (FIGS. 22-23). In one embodiment, the extension member 605 is configured as a liposuction probe and ranges in diameter from about 1 mm to 10 mm. In another embodiment, extension member 605 is configured for extraction of intervertebral disc material and ranges in diameter from about 1 mm to 5 mm. As can be seen in FIG. 23, the outlets 625 for introducing the vapor into an interface with tissue are disposed in the distal termination region 626 of aspiration lumen 615. The outlets 625 in FIG. 23 are shown as round ports hut also can be elongated and/or arcuate as shown in FIGS. 24A and 24B. As can be seen in FIG. 23, the outlets 625 are positioned distance D from the distalmost surface 628 of the extension member 605 which can range from about 0.1 mm to 5 mm inward of surface 628. The number of outlets 625 can range from about 2 to 20 and can have any suitable cross-section to fit in a particular dimension of aspiration channel 615. Of particular interest, referring to FIG. 23, the axis 630 of each outlet 625 that extends through inner wall 624 of the extension member is angled proximally to thereby eject vapor media more in line with the flow direction induced by aspiration forces. In another embodiment as shown in FIG. 25, the axis 630 of each outlet 625 extending through inner wall 624 of extension member 605 also in angled radially rather than being directed toward the axis of extension member 605. The radial angle of outlet 625 as shown in FIG. 25 provides flows that create a vortex in combination with the aspiration forces.

In use, the probe 600 and system of FIGS. 22-25 can be used to extract soft tissue from the interior of a patient's body such as in a liposuction procedure. The aspiration forces suction soft tissue into die distal termination region 626 of aspiration lumen 615 wherein the high velocity injection of vapor media, which can be provided under pressure ranging from about 10 psi to 1,000 psi, will apply thermal energy in the vapor-to-liquid phase transition as well as some mechanical energy to thermally weaken and dissociate covalent bonds and dissolve and disintegrate the soft tissue. The continued aspiration forces then extract the tissue from the treatment site through channel 615. The method of the invention includes using the energy levels associated with the vapor injection to discriminate the type of tissue being disintegrated and extracted. For example, in removing a disc nucleus, the softer tissue of the nucleus can be extracted at selected vapor delivery parameters wherein the same parameters will not ablate and disintegrate adjacent annulus tissue. In another embodiment, the concentric flow channel 620 can carry at least one diffuser structure and/or NTCR structure with opposing polarity electrodes for vaporizing the liquid flow media rather than generating the vapor in the handle portion of the probe.

Figure 26:
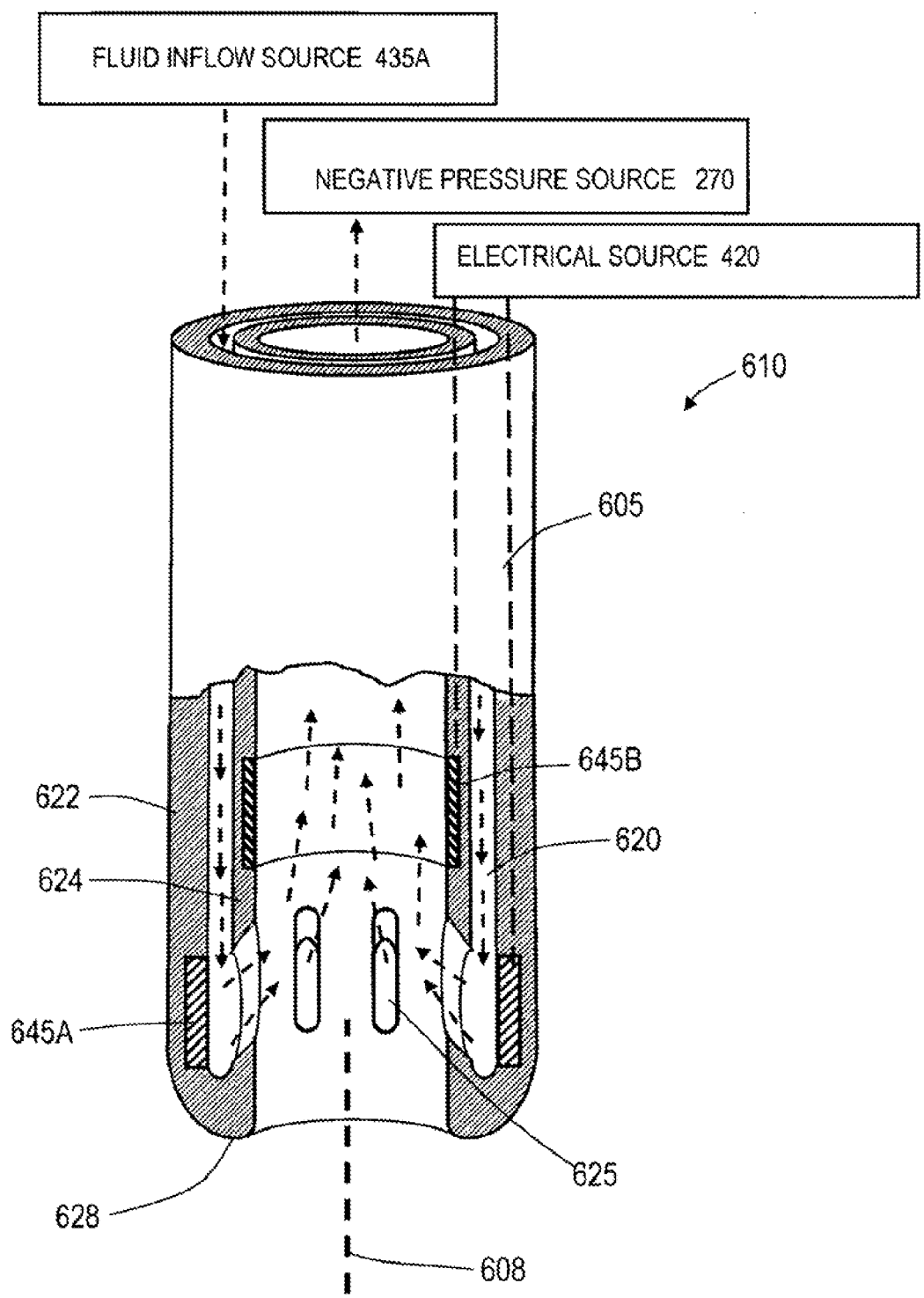
FIG. 26 is an enlarged cut-away view of another working end that carries at least one electrode for delivering energy to tissue or vapor media flows.

In another embodiment in FIG. 26, a distal region 640 (and optionally other more proximal regions) of the aspiration channel 615 carry at least one electrode coupled to an electrical source 420 that is adapted to deliver sufficient voltage to the vapor and/or tissue in channel to further ablate the tissue. The embodiment of FIG. 26 includes concentric first polarity electrode 645A and second polarity electrode 645B that are axially spaced apart, but the electrodes also can be spaced apart helically, radially or any combination thereof. One of the electrodes can disposed in inflow channel 620 proximal to the flow outlets 625 as shown in FIG. 26, or both electrodes 645A and 645B can be in aspiration channel 615. The extension member 605 is fabricated of an insulative material or coated with an insulator to maintain electrical isolation between the electrodes as is known in the art. In one embodiment, the electrical source 420 is configured for applying sufficient voltage to non-ionized vapor media as it exits outlets 625 to provide the heat of ionization to convert the vapor to an ionized media or plasma for ablating tissue. Thus, the probe has a first or proximal energy deliver system for delivering the heat of vaporization and a second distal system for delivering the heat of ionization. The plasma then can be created in intervals or on-demand to disintegrate tissue.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A method for delivering energy to mammalian body structure, comprising:
   providing an elongated probe with a proximal end and a working end;
   providing a flow of a non-ionized flow media from at least one port in the working end, wherein a source of the non-ionized flow media is positioned remotely from the working end; and
   controlling ejection of the non-ionized flow media from the working end, wherein the non-ionized flow media carries sufficient thermal energy such that contact of the non-ionized flow media with mammalian body structure causes modification of the body structure through a phase change of the non-ionized flow media.

2. The method of claim 1 including providing the flow of non-ionized flow media from a needle-like working end into the body structure.

3. The method of claim 1 including providing the flow of non-ionized flow media from the working end into at least one of a body lumen, soft tissue, surface tissue and bone.

4. The method of claim 1 including providing the flow of non-ionized flow media in at least one of as distal direction relative to as probe axis, a proximal direction relative the said axis and substantially perpendicular to said axis.

5. The method of claim 4 including providing the flow of non-ionized flow media from at least one proximally-oriented port into said interior channel in the probe.

6. The method of claim 5 including providing negative pressure aspiration forces to said interior channel in the probe.

7. The method of claim 1 wherein the source of the non-ionized flow media is positioned at least 5 mm; 10 mm and 100 mm from a surface of the working end.

* * * * *